United States Patent
Lynch et al.

(10) Patent No.: US 9,549,906 B2
(45) Date of Patent: Jan. 24, 2017

(54) COMPOSITIONS AND METHODS FOR TREATMENT OF OCULAR INFLAMMATION AND/OR PAIN

(71) Applicants: Mary Lynch, Halifax (CA); Melanie Kelly, Halifax (CA)

(72) Inventors: Mary Lynch, Halifax (CA); Melanie Kelly, Halifax (CA)

(*) Notice: Subject to any disclaimer, the term of this patent is extended or adjusted under 35 U.S.C. 154(b) by 11 days.

(21) Appl. No.: 14/722,991

(22) Filed: May 27, 2015

(65) Prior Publication Data
US 2015/0258040 A1    Sep. 17, 2015

Related U.S. Application Data

(63) Continuation-in-part of application No. PCT/CA2014/000841, filed on Nov. 20, 2014.
(Continued)

(51) Int. Cl.
*A61K 31/09*     (2006.01)
*A61K 31/05*     (2006.01)
*A61K 31/015*    (2006.01)
*A61K 45/06*     (2006.01)
*A61K 31/01*     (2006.01)

(52) U.S. Cl.
CPC .............. *A61K 31/05* (2013.01); *A61K 31/01* (2013.01); *A61K 31/015* (2013.01); *A61K 31/09* (2013.01); *A61K 45/06* (2013.01)

(58) Field of Classification Search
CPC ..................................................... A61K 31/09
See application file for complete search history.

(56) References Cited

U.S. PATENT DOCUMENTS 7,618,966 B2   11/2009   Chen et al.
8,293,786 B2   10/2012   Stinchcomb et al.
(Continued)

FOREIGN PATENT DOCUMENTS

WO   2007052013 A1   5/2007
WO   2010041253 A1   4/2010
(Continued)

OTHER PUBLICATIONS

Bioorganic & Medicinal Chemistry 22 (2014) 3245-3251.*
(Continued)

*Primary Examiner* — Benjamin Packard
(74) *Attorney, Agent, or Firm* — Bereskin & Parr LLP/S.E.N.C.R.L., s.r.l.; Noel Courage

(57) ABSTRACT

The disclosure provides methods of treatment of ocular inflammation and/or neuropathic pain in a subject in need thereof, comprising administering to the subject in need thereof a CB2 target agent, a cannabimimetic agent or a combination thereof. The agent is optionally a cannabinoid, such as a non-psychotropic cannabinoid or a synthetic cannabinoid. In certain embodiments, the non-psychotropic phytocannabinoid is β-caryophyllene or cannabidiol [CBD] and the synthetic cannabinoid is HU-433, HU-308, or a modified CBD such as CBD-DMH. In methods of the disclosure, CBD-DMH is optionally administered in combination with a further CB2 target agent or cannabimimetic agent. The disclosure also provides ocular pharmaceutical compositions containing the CB2 target agents and/or cannabimimetic agents described herein.

23 Claims, 18 Drawing Sheets

Related U.S. Application Data

(60) Provisional application No. 61/906,694, filed on Nov. 20, 2013.

(56) References Cited

U.S. PATENT DOCUMENTS

| | | | |
|---|---|---|---|
| 2004/0186166 A1* | 9/2004 | Burstein et al. | 514/454 |
| 2007/0082954 A1* | 4/2007 | Mechoulam et al. | 514/568 |
| 2009/0247619 A1 | 10/2009 | Stinchcomb et al. | |
| 2010/0273895 A1 | 10/2010 | Stinchcomb et al. | |
| 2012/0202891 A1 | 8/2012 | Stinchcomb et al. | |

FOREIGN PATENT DOCUMENTS

| | | |
|---|---|---|
| WO | 2010127033 A1 | 11/2010 |
| WO | 2013009928 A1 | 1/2013 |

OTHER PUBLICATIONS

Liou, G.I., et al.—"Mediation of Cannabidiol anti-inflammation in the Retina by Equilibrative Nucleoside Transporter and A2A Adenosine Receptor", Invest. Ophthalmol. Vis. Sci., 2008, vol. 49(12), p. 5526-5531.
Liou, G.I.—"Diabetic retinopathy: Role of inflammation and potential therapies for anti-inflammation", World J Diabetes, 2010, vol. 1(1), p. 12-18.
Hingorani, T., et al.—"Ocular Disposition of the Hemiglutarate Ester Prodrug of Δ9-Tetrahydrocannabinol from Various Ophthalmic Formulations", Pharm. Res., 2013; 30(8), published online Jun. 5, 2013.
Toguri, J. T., et al.—"Cannabinoid modulation of leukocyte-endothelial interactions model of local inflammation of the eye (endotoxin-induced uveitis)"—page created May 9, 2012.
Toguri, J. T., et al. —"CB2 Receptor Activation is Anti-Inflammatory in an Endotoxin-Induced Uveitis Model" Proceedings of the British Pharmacological Society at http://www.pA2online.org/abstracts/Voll lIssuelabst004.pdf, page created Mar. 24, 2013.
Toguri, J.T., Szczeniak, A.M., Zhou, J., Lehmann, C., Kelly, M.E.M. "CB2 Receptor activation is anti-inflammatory in an endotoxin-induced uveitis model" [abstract]. For European Workshop on Cannabinoid Research (EWCR) conference. Apr. 18-21, 2013; Dublin, Ireland.
Toguri, J.T., Moxsom, R., Zhou, J., Cerny, V., Whynot, S. Kelly, M.E.M., Lehmann, Ch. "Effects of cannabinoid receptor modulation on leukocyte-endothelial interactions in endotoxin-induced uveitis" [abstract]. For International Cannabinoid Research Society (ICRS) conference: Jul. 5-11, 2011; Illinois, USA.
Lehmann, Ch. Moxsom, R., Toguri, T., Zhou, J., Cerny, V., Whynot, S., Hung, O., Shukla, R., Kelly, M. "Reciprocal modulation of the endocannabinoid system inhibits leukocyte activation during experimental sepsis" [abstract]. For International Anesthesia Research Society (IARS) Annual meeting; May 21-24, 2011; Vancouver, British Columbia, Canada.
Toguri, J.T., Szczeniak, A.M., Zhou, J., Lehmann, Ch. Kelly, M.E.M. "Cannabinoid modulation of leukocyte-endothelial interactions in an endotoxin-induced uveitis model" [abstract]. For International Cannabinoid Research Society (ICRS) conference. Jul. 22-27, 2012; Freibourg, Germany.
El. -Remessy A.B. et al., "Neuroprotective and Blood-Retinal Barrier-Preserving Effects of Cannabidiol in Experimental Diabetes", American Journal of Pathology, vol. 168, No. 1, Jan. 2006, pp. 235-244.
El.-Remessy A.B. et al., "Neuroprotective Effect of (-)Δ9-Tetrahydrocannabinol and Cannabidiol in N-Methyl-D-Aspartate-Induced Retinal Neurotoxicity", American Journal of Pathology, vol. 163, No. 5, Nov. 2003, pp. 1997-2008.
El.-Remessy A.B. et al., "Neuroprotective Effects of Cannabidiol in Endotoxin-Induced Uveitis: Critical Role of p38 MAPK Activation", Molecular Vision, 2008; 14: pp. 2190-2203, Dec. 3, 2008.
El.-Remessy A.B. et al., "Cannabidiol Protects Retinal Neurons by Preserving Glutamine Synthetase Activity in Diabetes", Molecular Vision, 2010; 16: pp. 1487-1495, Aug. 4, 2010.
Kelly, M. Dong, A., Toguri, T., Zhou, J., Cerny, V., Whynot, S., Hung, O., Lehmann, C. "Cannabinoid 2 Receptor Modulation in the iris microcirculation during experimental endotoxemia" [abstract]. In: PA2 Online E-journal of the British Pharmacological Society Winter meeting; Dec. 14-16, 2010; London, England: BPS; 2010. p. 67., Abstract nr 0106.
Agarwal R., Iezhitsa I., Agarwal P., Abdul Nasir N.A., Razali N., Alyautdin R., Ismail N.M., "Liposomes in topical ophthalmic drug delivery: an update." Drug Deliv. Aug. 12, 2014:1-17.
Belmonte, C., M. C. Acosta and J. Gallar (2004). "Neural basis of sensation in intact and injured corneas." Exp Eye Res 78(3): 513-525.
Berenbaum, M. C. (1989). "What is synergy?" Pharmacol Rev 41(2): 93-141.
Conway, B. R. (2008). "Recent patents on ocular drug delivery systems." Recent Pat Drug Deliv Formul 2(1): 1-8.
Christopoulos, A. and T. Kenakin (2002). "G protein-coupled receptor allosterism and complexing." Pharmacol Rev 54 (2): 323-374.
Daisuke Ito, Kortaro Tanaka, Shigeaki Suzuki, Tomohisa Dembo, and Yasuo Fukuuchi, "Enhanced Expression of Iba1, Ionized Calcium-Binding Adapter Molecule 1, After Transient Focal Cerebral Ischemia in Rat Brain" Stroke. 2001;32:1208-1215.
Davis MP. "Cannabinoids in pain management: CB1, CB2 and non-classic receptor ligands". Expert Opin Investig Drugs. Aug. 2014;23(8):1123-40.
Draize, J. H., G. Woodard and H. O. Calvery (1944). "Methods for the study of irritation and toxicity of substances applied topically to the skin and mucous membranes." J Pharmacol and Exp Therapeutics 82: 377-390.
Frenzel, E. M., K. A. Neely, A. W. Walsh, J. D. Cameron and D. S. Gregerson (1998). "A new model of proliferative vitreoretinopathy." Invest Ophthalmol Vis Sci 39(11): 2157-2164.
Fride E, Feigin C, Ponde DE, Breuer A, Hanus L, Arshaysky N, Mechoulam R. (2004). "(+)-Cannabidiol analogues which bind cannabinoid receptors but exert peripheral activity only." Eur J Pharmacol 506(2): 179-188.
Friedman, N. J. (2010). "Impact of dry eye disease and treatment on quality of life." Curr Opin Ophthalmol 21(4): 310-316.
Guindon J., Hohmann A.G., "Cannabinoid CB2 receptors: a therapeutic target for the treatment of inflammatory and neuropathic pain." British Journal of Pharmacology 2008;153:319-334.
Hanus, L. A. Breuer, S. Tchilibon, S. Shiloah, D. Goldenberg, M. Horowitz, R. G. Pertwee, R. A. Ross, M. R and E. Fride (1999). "HU-308: A specific agonist for CB2, a peripheral cannabinoid receptor." Proc Nat Acad Sci 96: 14228-14233.
Hohmann, A. G. and R. L. Suplita, 2nd (2006). "Endocannabinoid mechanisms of pain modulation." AAPS J 8(4): E693-708.
Hsieh, G. C., M. Pai, P. Chandran, B. A. Hooker, C. Z. Zhu, A. K. Salyers, E. J. Wensink, C. Zhan, W. A. Carroll, M. J. Dart, B. B. Yao, P. Honore and M. D. Meyer (2011). "Central and peripheral sites of action for CB(2) receptor mediated analgesic activity in chronic inflammatory and neuropathic pain models in rats." Br J Pharmacol 162(2): 428-440.
Hughes, P. M., O. Olejnik, J. E. Chang-Lin and C. G. Wilson (2005). "Topical and systemic drug delivery to the posterior segments." Adv Drug Deliv Rev 57(14): 2010-2032.
Jabs, D. A., R. B. Nussenblatt and J. T. Rosenbaum (2005). "Standardization of uveitis nomenclature for reporting clinical data. Results of the First International Workshop." Am J Ophthalmol 140(3): 509-516.
Laprairie RB, Bagher AM, Kelly MEM, Dupré DJ, Denovan-Wright EM (2014). "Type 1 Cannabinoid Receptor Ligands Display Functional Selectivity in a Cell Culture Model of Striatal Medium Spiny Projection Neurons." J Biol Chem, Sep. 5, 2014;289(36):24845-62.
Lee, R. W. and A. D. Dick (2012). "Current concepts and future directions in the pathogenesis and treatment of non-infectious intraocular inflammation." Eye (Lond) 26(1): 17-28.
Ley, K., C. Laudanna, M. I. Cybulsky and S. Nourshargh (2007). "Getting to the site of inflammation: the leukocyte adhesion cascade updated." Nat Rev Immunol 7(9): 678-689.

(56) References Cited

OTHER PUBLICATIONS

Lobo, C. (2012). "Pseudophakic cystoid macular edema." Ophthalmologica 227(2): 61-67.
Loftsson, T. and D. Duchene (2007). "Cyclodextrins and their pharmaceutical applications." Int J Pharm 329(1-2): 1-11.
Loftsson, T. and E. Stefánsson (2002). "Cyclodextrins in eye drop formulations: enhanced topical delivery of corticosteroids to the eye." Acta Ophthalmol Scand 80(2): 144-150.
Maestrelli, F., M. L. Gonzalez-Rodriguez, A. M. Rabasco, C. Ghelardini and P. Mura (2010). "New "drug-in cyclodextrin-in deformable liposomes" formulations to improve the therapeutic efficacy of local anaesthetics." Int J Pharm 395(1-2): 222-231.
Maestrelli, F., M. L. Gonzalez-Rodriguez, A. M. Rabasco and P. Mura (2005). "Preparation and characterisation of liposomes encapsulating ketoprofen-cyclodextrin complexes for transdermal drug delivery." Int J Pharm 298(1): 55-67.
McPartland, J. M. and E. B. Russo (2001). "Cannabis and cannabis extracts, greater than the sum of their parts?" J Cannabis Ther 1(3-4): 103-132.
Mechoulam, R. and Hanus, L. (2002). "Cannabidiol: an overview of some chemical and pharmacological aspects. Part I: chemical aspects." Chem Phys Lipids 121(1-2): 35-43.
Natarajan J.V., Ang M., Darwitan A., Chattopadhyay S., Wong T.T., Venkatraman S.S., "Nanomedicine for glaucoma: liposomes provide sustained release of latanoprost in the eye." Int J Nanomedicine. 2012;7:123-31.
Pertwee R.G., "The diverse CB1 and CB2 receptor pharmacology of three plant cannabinoids: Δ9-tetrahydrocannabinol, cannabidiol and Δ9-tetrahydrocannabivarin". British Journal of Pharmacology 2008;153:199-215.
Pertwee R.G., "Emerging strategies for exploiting cannabinoid receptor agonists as medicines." British Journal of Pharmacology 2009;156:397-411.
Pertwee R.G., "Targeting the endocannabinoid system with cannabinoid receptor agonists: pharmacological strategies and therapeutic possibilities." Phil. Trans. R. Soc. B 2012;367:3353-3363.
Pflugfelder, S. C. (2008). "Prevalence, burden, and pharmacoeconomics of dry eye disease." Am J Manag Care 14(3 Suppl): S102-106.
Rahn, E. J. and A. G. Hohmann (2009). "Cannabinoids as pharmacotherapies for neuropathic pain: from the bench to the bedside." Neurotherapeutics 6(4): 713-737.
Ranta, V. P. and A. Urtti (2006). "Transscleral drug delivery to the posterior eye: prospects of pharmacokinetic modeling." Adv Drug Deliv Rev 58(11): 1164-1181.
Rosenthal, P., I. Baran and D. S. Jacobs (2009). "Corneal pain without stain: is it real?" Ocul Surf 7(1): 28-40.
Rosenthal, P. and D. Borsook (2012). "The corneal pain system. Part I: the missing piece of the dry eye puzzle." Ocul Surf 10(1): 2-14.
Russo, E. B. (2011). "Taming THC: potential cannabis synergy and phytocannabinoid-terpenoid entourage effects." Br J Pharm 163: 1344-1364.
Sanz, M. J. and P. Kubes (2012). "Neutrophil-active chemokines in in vivo imaging of neutrophil trafficking." Eur J Immunol 42(2): 278-283.
Souto, E. B., S. Doktorovova, E. Gonzalez-Mira, M. A. Egea and M. L. Garcia (2010). "Feasibility of lipid nanoparticles for ocular delivery of anti-inflammatory drugs." Curr Eye Res 35(7): 537-552.

Straiker AJ, Maguire G, Mackie K, Lindsey J. "Localization of cannabinoid CB1 receptors in the human anterior eye and retina." Invest Ophthalmol Vis Sci. 1999;40:2442-8.
Szczesniak, A. M., M. E. Kelly, S. Whynot, P. N. Shek and O. Hung (2006). "Ocular hypotensive effects of an intratracheally delivered liposomal delta9-tetrahydrocannabinol preparation in rats." J Ocul Pharmacol Ther 22(3): 160-167.
Szczesniak A, Kelly MEM (2012). "Role of CB2 receptor in experimental uveoretinitis." International Cannabinoid Research Society 22nd Annual International Symposium on Cannabinoids, Frieburg, Germany.
Szczesniack A, Kelly MEM (2013). "Role of CB2 receptor in experimental proliferative vitreoretinopathy." International Cannabinoid Research Society 23rd Annual International Symposium on Cannabinoids., Vancouver, BC.
Thumma, S., S. Majumdar, M. A. Elsohly, W. Gul and M. A. Repka (2008). "Preformulation studies of a prodrug of Delta9-tetrahydrocannabinol." AAPS PharmSciTech 9(3): 982-990.
Toguri, J. T., C. Lehmann, R. B. Laprairie, A. M. Szczesniak, J. Zhou, E. M. Denovan-Wright and M. E. Kelly (2014). "Anti-inflammatory effects of cannabinoid CB(2) receptor activation in endotoxin-induced uveitis." Br J Pharmacol 171 (6): 1448-1461.
Wagner, H. and G. Ulrich-Merzenich (2009). "Synergy research: approaching a new generation of phytopharmaceuticals." Phytomedicine 16(2-3): 97-110.
Ward, S. J., M. D. Ramirez, H. Neelakantan and E. A. Walker (2011). "Cannabidiol prevents the development of cold and mechanical allodynia in paclitaxel-treated female C57Bl6 mice." Anesth Analg 113(4): 947-950.
Wenk, H. N. and C. N. Honda (2003). "Silver nitrate cauterization: characterization of a new model of corneal inflammation and hyperalgesia in rat." Pain 105(3): 393-401.
Yang Y., Yang H., Wang Z., Varadaraj K., Kumari S.S., Mergler S., Okada Y., Saika S., Kingsley P.J., Marnette L.J., Reinach P.S., "Cannabinoid receptor 1 suppresses transient receptor potential vanilloid 1-induced inflammatory responses to corneal injury". Cell Signal. 2013;25(2):501-511.
Yawn, B. P., P. C. Wollan, J. L. St Sauver and L. C. Butterfield (2013). "Herpes zoster eye complications: rates and trends." Mayo Clin Proc 88(6): 562-570.
Recht et al., "Antitumor effects of ajulemic acid (CT3), a synthetic non-psychoactive cannabinoid" Biochemical Pharmacology 2001, 62, pp. 755-763.
Karst et al., "Analgesic effect of the synthetic cannabinoid CT-3 on chronic neuropathic pain: A randomized controlled trial" JAMA 2003, 290(13), pp. 1757-1762.
Liu et al., "Activation and binding of peroxisome proliferator-activated receptor gamma by synthetic cannabinoid ajulemic acid" Molecular Pharmacology 2003, 63, pp. 983-992.
Burstein et al., "Ajulemic acid: A novel cannabinoid produces analgesia without a 'high'" Life Sciences 2004, 75, pp. 1513-1522.
Burstein, "The cannabinoid acids, analogs and endogenous counterparts" Bioorg Med Chem 2014, 22(10), pp. 2830-2843.
Tepper et al., "Ultrapure ajulemic acid has improved CB2 selectivity with reduced CB1 activity" Bioorg Med Chem 2014, 22, pp. 3245-3251.
Xiong et al., "Cannabinoids suppress inflammatory and neuropathic pain by targeting alpha3 glycine receptors" Journal of Experimental Medicine May 14, 2012, vol. 209, pp. 1121-1134.
Nagarkatti et al., "Cannabinoids as novel anti-inflammatory drugs" Future Medicinal Chemistry 2009, vol. 1, pp. 1333-1349.

* cited by examiner

C

A

B

C

D

COMPOSITIONS AND METHODS FOR TREATMENT OF OCULAR INFLAMMATION AND/OR PAIN

CROSS-REFERENCE TO RELATED APPLICATIONS

The present application is a continuation-in-part that claims the benefit of priority from PCT Patent Application No. PCT/CA2014/000841 filed on Nov. 20, 2014, which claims the benefit of priority from U.S. provisional application No. 61/906,694 filed on Nov. 20, 2013, the contents of both of which are incorporated herein by reference in their entirety.

FIELD OF THE DISCLOSURE

The disclosure provides compositions and methods for treating ocular pain and/or inflammation.

BACKGROUND

There is a need for novel treatments for pain and inflammation. The current agents are inadequate and can, for example, cause unacceptable side effects. Additionally, the growing concern about the potential for addiction with opioid pain treatment further supports the need for new pain therapies. In particular, there is a need for new products for the treatment of ocular neuropathic pain (e.g. corneal neuropathic pain) and/or inflammation (e.g. uveitis).

Cannabinoids have been used for systemic treatment of pain and inflammation. All of the cannabinoids currently sold for human use also exhibit cannabinoid receptor type 1 (CB1) effects which are associated with, for example, hypothermia, catalepsy, hypolocomotion and psychoactive effects so these agents are associated with sedation and other effects that may limit, for example, systemic dosing.

Both $CB_1$ and $CB_2$ receptors have been reported to be upregulated following trauma and inflammation (Pertwee 2008; 2009; 2012; Guindon and Hohmann, 2008). Activation of downstream pathways associated with these receptors is analgesic, anti-inflammatory and, in the case of $CB_1$, can promote cellular proliferation and wound healing (Yang, 2013).

CBD-DMH, like its parent molecule, cannabidiol (CBD), is non-psychotropic and exhibits analgesic and anti-inflammatory effects in animal models. However, CBD-DMH is reported to be more than 10-fold more potent than CBD. The structure of CBD and CBD-DMH have been previously described (Mechoulam et al., 2002; Fride et al., 2004).

HU-308 is a synthetic cannabinoid compound that binds and activates the CB2 receptor specifically (Hanus 1999). An enantiomeric derivative of HU-308, named HU-433, is also a CB2 agonist. HU-433 has been shown to have 2-3 orders of magnitude greater potency in both in vitro and in vivo systems. It shows no psychoactivity. The chemical structures of HU-308 and HU-433 were previously described in PCT Publication No. WO 2010/041253.

Without being bound by theory, *cannabis* synergy arises from constituent combination effects (Berenbaum 1989; McPartland and Russo 2001; Russo 2011). This may occur via several mechanisms including but not limited to: multi-target effects (receptor agonism or antagonism, anti-oxidant, modulation of endogenous endocannabinoid synthesis or metabolism, etc.), improved pharmacokinetic properties of compounds via modulation of solubility, bioavailability, as well as potential bacteriostatic activity (Wagner and Ulrich-Merzenich 2009; Russo 2011). CBD synergy with other phytocannabinoids and terpenoids from *Cannabis* has been reported specifically with regard to the treatment of inflammation and pain (Russo, 2011).

Inflammatory eye diseases represent a particular challenge due, for example, to risk of vision loss and blindness. The conditions encompass intraocular inflammation (e.g. uveitis, uveoretinitis, proliferative vitreoretinopathy) as well as extraocular inflammation, including corneal inflammation and neuropathology.

Collectively, ocular inflammation contributes significantly to the global incidence of blinding eye disease and can be a debilitating condition with a high medical and economic burden on populations.

Neuropathic Pain

Neuropathic pain is generated by pathology in the peripheral or central nervous system. A large number of disorders can give rise to neuropathic pain. This may range from nerves being cut (trauma or surgery) or damaged by viruses, ischemic and metabolic injury or complex genetic disorders to name a few. Neuropathic pain may arise from local damage to neural tissues as well as tissues remote to initial trauma and may also arise as a result of chronic inflammatory disease. Pharmacological management is one of the most used pain treatment options but results are poor with many patients obtaining inadequate relief with currently available agents. There is therefore a need for new agents for treatment of neuropathic pain. Neuropathic pain may affect any part of the body including the eye for which there are no adequate treatments at present.

Intraocular Inflammation and Optional Pain

Uveitis is a term used to describe any intraocular inflammation within the eye from the uvea (iris, ciliary body and choroid) to the sclera, retina and optic nerve. It involves either infectious or non-infectious conditions, which can be localized within the eye or associated with systemic inflammatory and autoimmune diseases, including reactive arthritis and multiple sclerosis. The most common form of uveitis, anterior uveitis, with inflammation of the iris and ciliary body, is additionally associated with considerable pain and photophobia (Jabs, Nussenblatt et al. 2005; Lee and Dick 2012). Untreated uveitis can lead to permanent loss of vision. Severe uveitis is treated aggressively to mitigate the damage caused by inflammation. However, currently utilized agents, including the "gold-standard" corticosteroids, anti-metabolites, biologic response modifiers and non-steroidal anti-inflammatory agents, suffer from significant side-effects and in some cases escalating costs (i.e. biologics). A search for newer efficacious, safe and/or cost-effective anti-inflammatory and immunomodulatory agents, suitable for acute and chronic use, either as sole treatments or in combination, and delivered locally to the eye, is a priority for the future treatment of ocular inflammation in order to prevent loss of vision.

Anterior uveitis (iritis) is associated with inflammation of iris and anterior tissues and this leads to pain and light sensitivity with pupillary changes in response to light. Anterior uveitis pain is typically resolved when the inflammation is treated so is not classed as neuropathic pain. Generally uveitis represents hyperactivation of the body's immune system; a form of local sepsis. Inflammatory conditions are represented by activation, recruitment, and migration of immune cells, release of proinflammatory cytokines, swelling, oedema and/or tissue damage. In posterior uveitis, this can also include gliosis, and activation of resident immune cells (microglia). In some retinal inflammatory diseases, cell proliferation with subsequent fibrosis and retinal detachment is present (i.e. proliferative vitreoretinopathy).

Posterior uveitis is not clinically associated with pain. Generally conditions with moderate or mild chronic inflammation in the retina do not present with pain but can result in loss of retinal neurons and vision loss. These include: posterior uveitis, retinitis and proliferative vitreoretinopathy.

Extraocular Inflammation and Pain

Corneal neuropathic hyperalgesia involves a dysfunctional corneal pain system and is associated with significant discomfort and persistent heightened sensitivity of the cornea (peripheral sensitization) in the absence of overt trauma or noxious stimuli (reviewed in Belmonte et al., 2004; Rosenthal & Borsook, 2012; Rosenthal et al., 2009). Ongoing excitation of corneal nerves, following corneal damage or irritation, results in the release of neuropeptides and inflammatory mediators that augment the inflammatory reaction (neurogenic inflammation) leading to hyperalgesia. Corneal hypersensitivity, neuroinflammation, pain and photophobia are reported in patients following refractive surgery and chemical/toxic exposure, including repetitive use of benzalkonium chloride-preserved eye drops. Corneal neuropathic pain is also a central pathogenic feature of eye disorders that are collectively referred to as dry eye, and include non-infectious immunological causes such as Sjogren syndrome and systemic lupus as well as infections with Herpes Zoster (reviewed in Rosenthal & Borsook, 2012; Yawn et al., 2013). Up to 20% of adults aged 45 or older are affected by dry eye disease presenting a major health concern with significant economic and societal implications (reviewed in Friedman, 2013; Pflugfelder, 2008). In many cases dry eye disease is refractory to treatment and lacking in a clear association between symptoms and signs. For example, while inflammatory corneal hyperalgesia, as a result of ocular surface desiccation (evaporation dry eye), is the most common form of corneal hyperalgesia, many patients who report dry eye symptoms do not show signs of dry eyes (reduced tears), or superficial corneal erosions. Contrasted are others who have insufficient tear quantity and quality who are asymptomatic. Furthermore, neuropathic disease can sometimes precede alterations in tear film dynamics (Rosenthal & Borsook, 2012; Rosenthal et al., 2009).

Current agents prescribed for corneal neuropathic pain include a wide variety of distinct compounds such as but not limited to, opioids, non-steroidal anti-inflammatory drugs, sodium channel blockers (local anesthetics), anti-convulsants, tricyclic anti-depressants and GABAergic agents. However, present pharmacotherapy remains inadequate and the complex nature of corneal neuropathic pain is highlighted by the fact that no single known treatment appears to be effective in managing symptoms. Furthermore, the undesirable side-effects of many currently prescribed agents limit the therapeutic window for treatment. Corneal inflammatory neuropathic pain therefore represents a significant unmet therapeutic need (Rosenthal & Borsook, 2012; Rosenthal et al., 2009).

CBD, or CBD in combination with other endocannabinoid system modulators, has proven clinical and pre-clinical efficacy in the treatment of neuropathic pain resulting from nerve injury and disease (Hsieh et al., 2011; Ward et al., 2011; reviewed in Rahn and Hohmann 2009; Hohman & Suplita, 2006).

SUMMARY

The present disclosure provides anti-inflammatory and immunomodulatory agents, suitable for acute and chronic use, either as sole treatments or in combination, and for delivery locally to the eye. Agents are optionally used for treatment (including prevention) of ocular inflammation optionally preventing associated pain and/or loss of vision.

Cannabinoids, such as the CB2 agonists HU-308, HU-433 and CBD possess anti-inflammatory properties. The present disclosure provides methods for ocularly administering such compounds for reducing ocular inflammation and pain in a subject. Non-psychotropic phytocannabinoids, (e.g. β-caryophyllene, cannabidiol [CBD]), and synthetic cannabinoids (e.g. HU-433, HU-308, CBD-DMH) are useful ocularly for the treatment of ocular inflammation and neuropathic pain. Without being bound by theory, these products are directed at the endocannabinoid system (ECS). The ECS is a complex and sophisticated network that is part of the body's pain and immune defence network. There are two main receptor types in the ECS. These are the CB1 and the CB2 receptors respectively. The CB2 receptors are located primarily in the peripheral tissues (e.g. skin, eye, skeleton, viscera) and in neural glial cells (brain immune defence cells). The ECS is an emerging useful target for treating pain and inflammation.

Accordingly, the present disclosure includes a method of treating ocular inflammation and/or ocular neuropathic pain in a subject in need thereof, comprising administering ocularly to the subject a CB2 target agent, a cannabimimetic agent or a combination thereof.

In an embodiment, the CB2 target agent comprises a CB2 agonist agent, a CB2 partial agonist agent, a CB2 positive allosteric modulator or a combination thereof. In another embodiment, the CB2 target agent is CBD-DMH.

In an embodiment, the method comprises administering the CBD-DMH in combination with at least one further CB2 target agent. In another embodiment, the at least one further CB2 target agent is HU 433, HU 308, β-caryophyllene, CBD or combinations thereof.

In an embodiment, the method comprises administering the CBD-DMH in combination with at least one further cannabimimetic agent. In another embodiment, the at least one further cannabimimetic agent is a non-selective cannabinoid receptor agonist. In a further embodiment, the non-selective cannabinoid receptor agonist is selected from $\Delta^8$-THC or a prodrug thereof, $\Delta^9$-THC or a prodrug thereof, CP 55,940, WIN 55,212-2 and combinations thereof.

In an embodiment, the method is a method of treating ocular inflammation caused by a non-infectious condition.

In an embodiment, the condition is selected from posterior uveitis, retinitis, uveoretinitis and proliferative vitreoretinopathy. In an alternative embodiment, the ocular inflammation further presents with non-neuropathic pain and the treatment reduces the pain. In another embodiment of the present disclosure, the condition is selected from anterior uveitis, episcleritis and scleritis.

In another embodiment of the present disclosure, the ocular inflammation is intraocular inflammation.

In an embodiment, the method is a method for treating ocular neuropathic pain and ocular inflammation caused by a non-infectious condition. In another embodiment of the present disclosure, the ocular neuropathic pain is corneal neuropathic pain. In a further embodiment, the ocular neuropathic pain arises from dry eye, trauma, a corneal abrasion, a corneal burn, a corneal transplant, an autoimmune disease or an allergen.

The present disclosure also includes an ocular pharmaceutical composition comprising a CB2 target agent, a cannabimimetic agent or a combination thereof and a carrier suitable for ocular administration to an eye.

In an embodiment, the composition comprises CBD-DMH.

In another embodiment, the composition comprises at least one further CB2 target agent. In a further embodiment, the composition further comprises at least one further cannabimimetic agent.

In an embodiment, the carrier comprises a liposome.

The present disclosure also includes a method of treating ocular inflammation or ocular neuropathic pain in a subject in need thereof, comprising administering ocularly to the subject a CB2 target agent, a cannabimimetic agent or a combination thereof, optionally wherein the cannabimimetic agent is a non-psychotropic cannabimimetic agent.

In an embodiment, the subject is administered a CB2 target agent, and the CB2 target agent is a CB2 agonist agent, a CB2 partial agonist agent, a CB2 positive allosteric modulator or a combination thereof. In another embodiment, the CB2 agonist agent is HU-433, HU-308 or β-caryophyllene; the CB2 partial agonist agent is CBD; and the CB2 positive allosteric modulator is CBD-DMH. In a further embodiment of the present disclosure, the subject is ocularly administered CBD-DMH.

In an embodiment, the CB2 target agent or the cannabimimetic agent is a cannabinoid. In another embodiment, the cannabinoid is a non-psychotropic cannabinoid, optionally wherein the non-psychotropic cannabinoid is a phytocannabinoid, a synthetic cannabinoid or a combination thereof.

In a further embodiment, the phytocannabinoid is β-caryophyllene, cannabidiol or a combination thereof; and the synthetic cannabinoid is HU-433, HU-308, a modified CBD or a combination thereof, optionally wherein the modified CBD is CBD-DMH.

In an embodiment of the present disclosure, the method is a method of treating ocular inflammation. In an embodiment, the ocular inflammation is caused by an eye disease. In another embodiment, the eye disease causes intraocular inflammation. Optionally the eye disease is uveitis, uveoretinitis or proliferative vitreoretinopathy. In another embodiment, the eye disease causes extraocular inflammation. Optionally, the eye disease is corneal inflammation or neuropathology.

In an embodiment of the present disclosure, the subject has an eye disease that causes pain and loss of vision, and the agent reduces the pain and/or reduces the loss of vision.

In another embodiment of the present disclosure, the method is a method of treating ocular neuropathic pain.

In an embodiment, the subject is a mammal, optionally a human.

The present disclosure also includes an ocular pharmaceutical composition comprising a CB2 target agent, a cannabimimetic agent or a combination thereof and a carrier suitable for ocular administration to an eye, optionally wherein the cannabimimetic agent is a non-psychotropic cannabimimetic agent.

In an embodiment, the composition comprises a CB2 target agent, and the CB2 target agent is a CB2 agonist agent, a CB2 partial agonist agent, a CB2 positive allosteric modulator or a combination thereof. In another embodiment, the CB2 agonist agent is HU-433, HU-308 or β-caryophyllene; the CB2 partial agonist agent is CBD; and the CB2 positive allosteric modulator is CBD-DMH. In a further embodiment of the present disclosure, the composition comprises CBD-DMH.

In an embodiment, the CB2 target agent or the cannabimimetic agent is a cannabinoid. In another embodiment, the cannabinoid is a non-psychotropic cannabinoid, optionally wherein the non-psychotropic cannabinoid is a phytocannabinoid, a synthetic cannabinoid or a combination thereof.

In a further embodiment, the phytocannabinoid is β-caryophyllene, cannabidiol or a combination thereof; and the synthetic cannabinoid is HU-433, HU-308, a modified CBD or a combination thereof, optionally wherein the modified CBD is CBD-DMH.

In an embodiment, the carrier comprises a liposome. In another embodiment, the carrier comprises an oil-in-water emulsion formulation.

The present disclosure also includes a method of treating ocular inflammation or ocular neuropathic pain in a subject in need thereof, comprising administering to the subject in need thereof a CB2 agonist agent or non-psychotropic cannabimimetic agent.

In one embodiment, the agent is a cannabinoid. Optionally, the cannabinoid is a non-psychotropic cannabinoid, such as a phytocannabinoid, or a synthetic cannabinoid. In one embodiment, the non-psychotropic phytocannabinoid is β-caryophyllene or cannabidiol [CBD] and the synthetic cannabinoid is HU-433, HU-308 or CBD-DMH or a combination of two or more of the foregoing.

In one embodiment, the inflammation is caused by the subject having an eye disease. In an embodiment, the eye disease causes intraocular inflammation. In another embodiment, the eye disease causes extraocular inflammation. In yet another embodiment, the eye disease causes pain and loss of vision, and the agent reduces the pain and/or reduces the loss of vision.

In one embodiment, the eye disease is uveitis, uveoretinitis or proliferative vitreoretinopathy. In another embodiment, the eye disease is corneal inflammation or neuropathology.

In one embodiment, the CB2 agonist agent or non-psychotropic cannabimimetic agent is delivered locally to the eye.

In one embodiment, the subject is a mammal, optionally a human.

The present disclosure also includes an ocular pharmaceutical composition comprising a CB2 agonist agent or a non-psychotropic cannabimimetic agent and a carrier suitable for administration to eye.

In one embodiment, the composition comprises an agent that is a cannabinoid, optionally a non-psychotropic cannabinoid or a synthetic cannabinoid. The non-psychotropic cannabinoid is optionally a phytocannabinoid. In one embodiment, the non-psychotropic phytocannabinoid is β-caryophyllene or CBD and the synthetic cannabinoid is HU-433, HU-308, CBD-DMH, or a combination of two or more of the foregoing.

In one embodiment, the carrier comprises a liposome, optionally a cyclodextrin liposome.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

Corneal insult was left untreated (Corneal insult only; n=14), or treated with 3 doses of empty liposomes (Corneal insult+Liposomal Vehicle; n=14), or liposomal THC (Corneal insult+Liposomal THC; n=16). *P<0.05; **P<0.01.

Figure 15:
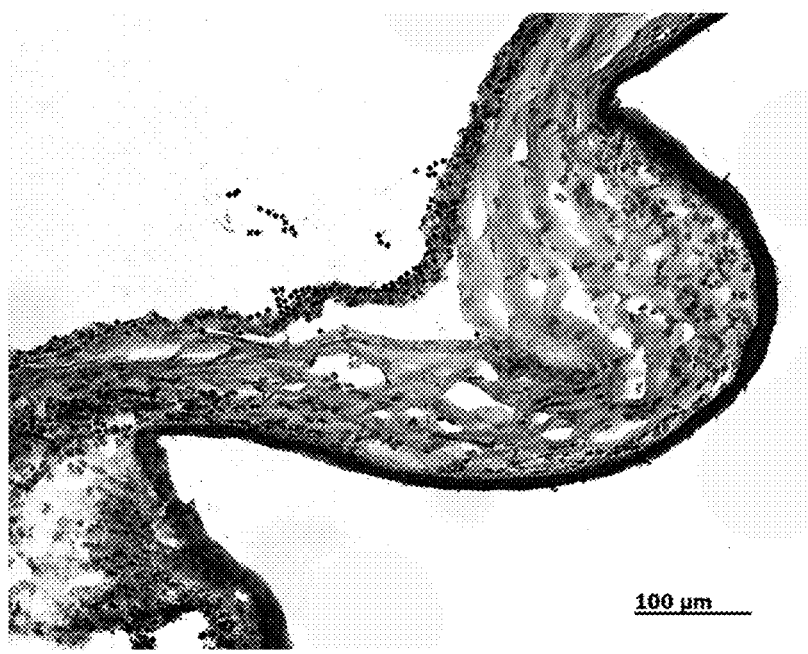
Figure 15:
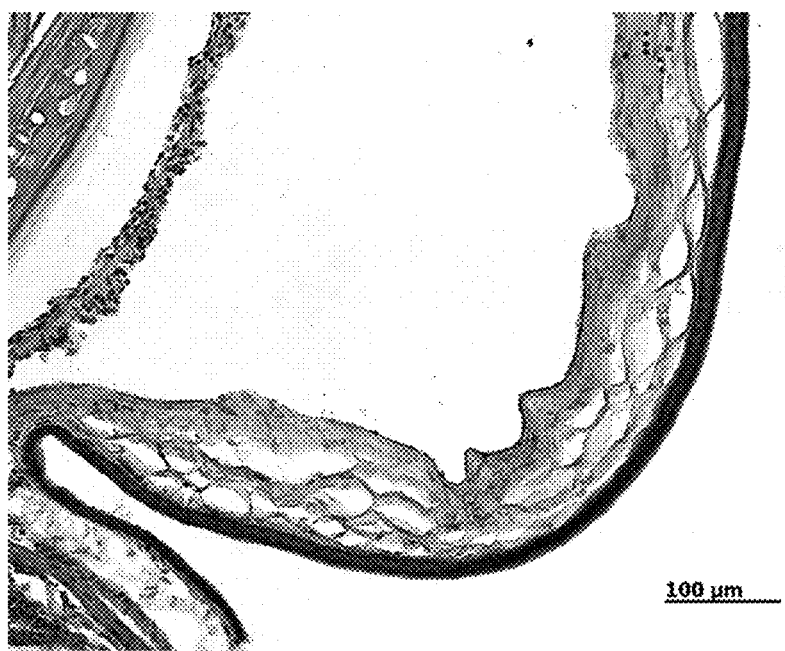
Figure 15:
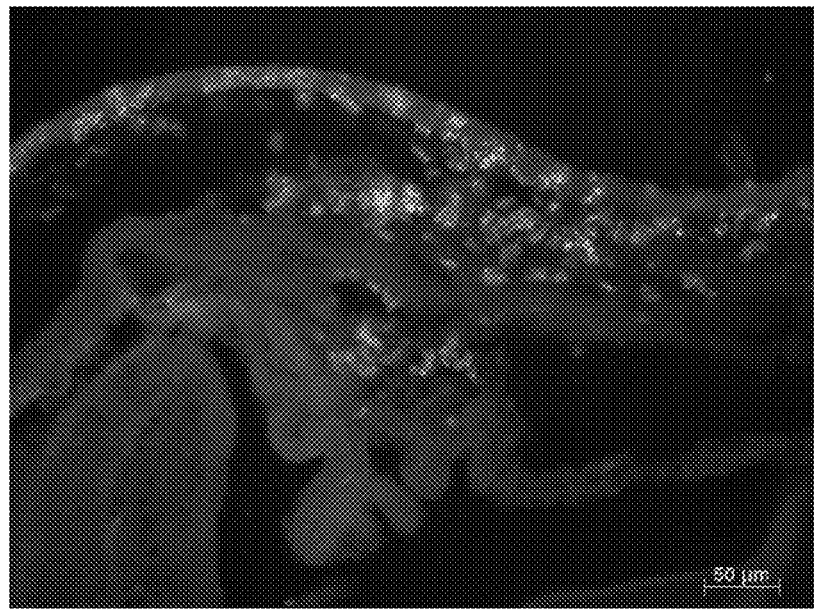
Figure 15:
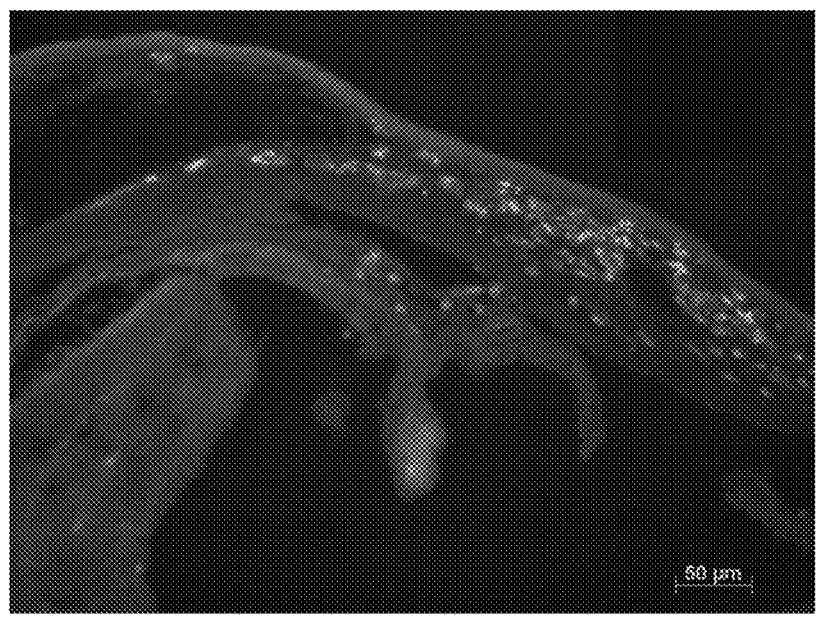

FIG. 15 shows exemplary images of a histological examination of the corneal edge region after silver nitrate chemical insult. A: Corneal edge region of untreated left eye removed post-mortem 12 hours after corneal insult (cauterization by silver nitrate). Scale Bar=100 µm. B: Right eye cornea treated with 3 doses of topical liposomal 0.1% THC and 2% CBD-DMH. Topical cannabinoids were administered at 30, 60 and 120 minutes after corneal insult by silver nitrate application. Scale Bar=100 µM. C: Corneal edge of untreated left eye stained with LY-6 antibody for visualizing neutrophils. Scale Bar=50 µm. D: Right eye cornea stained with LY-6 antibody and treated with 3 doses of topical liposomal 0.1% THC and 2% CBD-DMH administered at 30, 60 and 120 minutes after corneal insult by silver nitrate. Scale Bar=50 µm.

DETAILED DESCRIPTION

The disclosure relates to the use of a CB2 target agent, a cannabimimetic agent or a combination thereof, optionally a non-psychotropic cannabimimetic agent for treatment of ocular inflammation and/or ocular neuropathic pain in a subject. For example, the disclosure provides methods of treatment of ocular inflammation and/or ocular neuropathic pain in a subject in need thereof, comprising administering ocularly to the subject in need thereof a CB2 target agent and/or a cannabimimetic agent, optionally a non-psychotropic cannabimimetic agent. The agent is optionally a cannabinoid, such as a non-psychotropic cannabinoid or a synthetic cannabinoid. In certain embodiments, the non-psychotropic phytocannabinoid is a phytocannabinoid such as β-caryophyllene or cannabidiol [CBD] and the synthetic cannabinoid is HU-433, HU-308 or CBD-DMH. A combination of two or more of the foregoing may also be used for treatment. The CB2 target agent is optionally a CB2 agonist agent, a CB2 partial agonist agent or a CB2 positive allosteric modulator. The disclosure also provides ocular pharmaceutical compositions containing the CB2 target agents and/or cannabimimetic agents such as non-psychotropic cannabimimetic agents.

I. Definitions

The term "HU-433" as used herein refers to a synthetic cannabinoid agonist of the chemical structure:

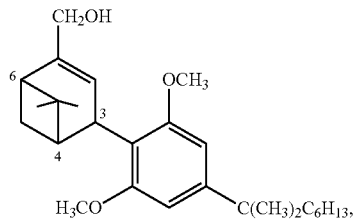

wherein the CIP configurations of the positions marked "3", "4" and "6" in the above chemical structure are R, R and R, respectively.

The term "HU-308" as used herein refers to a synthetic cannabinoid agonist of the chemical structure:

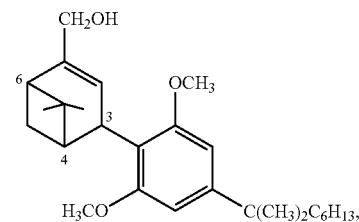

wherein the CIP configurations of the positions marked "3", "4" and "6" in the above chemical structure are S, S and S, respectively.

The terms "cannabidiol" or "CBD" as used herein refer to a non-psychotropic phytocannabinoid of the chemical structure:

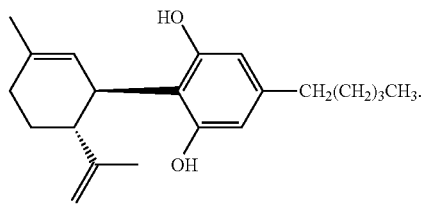

The term "CBD-DMH" as used herein refers to a synthetic cannabinoid of the chemical structure:

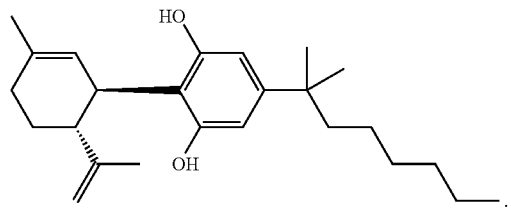 [SMILES: C=C(C)[C@@H]1CCC(C)=C[C@H]1c1c(O)cc(C(C)(C)CCCCCC)cc1O]

The terms "β-caryophyllene", "βc" or "Beta-C" as used herein refer to a non-psychotropic phytocannabinoid of the chemical structure:

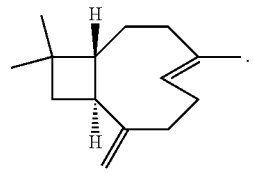

In embodiments of the present disclosure, the compounds described herein have at least one asymmetric center. Where compounds possess more than one asymmetric center, they may exist as diastereomers. It will also be appreciated that, for example, (+)-CBD and modified (+)-CBDs are known to be psychoactive; i.e. they may bind to the CB1 receptor.

The term "subject" as used herein includes all members of the animal kingdom including mammals, and suitably refers to humans.

II. Pharmaceutical Compositions

The present disclosure includes a composition comprising a CB2 target agent and/or a cannabimimetic agent such as a non-psychotropic cannabimimetic agent. Such agents are suitably formulated into ocular pharmaceutical compositions for ocular administration to subjects in a biologically compatible form suitable for ocular administration to an eye.

For example, solubility profile, partition coefficient, pH rate profile, $pK_a$, stability in pharmaceutical solvents, drug-excipient interaction and effect of moisture, temperature, light and oxygen on an agent such as Beta-C, CBD, CBD-DMH or other modified CBDs are determined. Optionally, all excipients used in the formulation are "Generally Regarded as Safe" (GRAS) and are approved by Food and Drug Administration (FDA) and Health Canada for ocular delivery. Biopharmaceutical characterization, analytical methods development, optimization and validation are also determined.

Accordingly, the present disclosure includes an ocular pharmaceutical composition comprising a CB2 target agent, a cannabimimetic agent (such as a non-psychotropic cannabimimetic agent) or a combination thereof and a carrier suitable for ocular administration to an eye.

The selection of a suitable agent such as a non-psychotropic phytocannabinoid and/or synthetic cannabinoid derivative for use in the compositions of the disclosure can be made by a person skilled in the art.

For example, both CBD and β-caryophyllene are useful as agents to treat pain and inflammation; they lack psychoactivity, and have a broad safety margin. Also useful for treating pain and inflammation is the CBD derivative, CBD dimethyl heptyl (CBD-DMH), a CBD analogue (also sometimes referred to herein as an example of a "modified CBD"). The synthetic cannabinoid HU-308 has shown useful anti-inflammatory action in pre-clinical models of uveitis and proliferative vitreoretinopathy and in experimental endotoxemia, where it decreases intestinal leukocyte adherence, improves intestinal capillary perfusion, reduces release of pro-inflammatory cytokines and reduces soluble adhesion molecule levels.

The inventors have obtained reduced inflammation in experimental models of ocular inflammation and pain. HU-433 is more potent than HU-308 in reducing ocular inflammation in experimental uveitis as well as mitigating inflammation in experimental models of sepsis. Models of neuropathic pain and painful inflammatory conditions of the eye are tested to show useful anti-pain and anti-inflammatory activity of HU-433.

It will be appreciated by a person skilled in the art that certain agents may fall under both the term "CB2 target agent" and the term "cannabimimetic agent" as those terms are used herein. For example, CBD-DMH is a CB2 positive allosteric modulator which is one example of a CB2 target agent as that term is used herein. CBD-DMH is also an example of a cannabimimetic agent as that term is used herein.

In an embodiment of the present disclosure, the active agent in the ocular pharmaceutical composition is a CB2 target agent. As used herein the term "CB2 target agent" refers to an agent that binds, activates and/or increases the activation of the CB2 receptor. Optionally, the CB2 target agent is a CB2 agonist agent, a CB2 partial agonist agent, a CB2 positive allosteric modulator or a combination thereof. It will be appreciated by a person skilled in the art that the term "CB2" as used herein in terms such as "CB2 target agent", "CB2 agonist agent", "CB2 partial agonist agent", "CB2 positive allosteric modulator" and the like refers to the CB2 receptor.

For example, the CB2 agonist agent can be HU-433, HU-308 or β-caryophyllene. For example, the CB2 partial agonist agent can be CBD. For example, the CB2 positive allosteric modulator can be CBD-DMH.

In an embodiment, the CB2 target agent or the cannabimimetic agent (such as a non-psychotropic cannabimimetic agent) is a cannabinoid. In another embodiment, the cannabinoid is a non-psychotropic cannabinoid. For example, the non-psychotropic cannabinoid can be a phytocannabinoid, a synthetic cannabinoid or a combination thereof.

In an embodiment of the present disclosure, the phytocannabinoid is β-caryophyllene, cannabidiol or a combination thereof. For example, the phytocannabinoid can be β-caryophyllene. For example, the phytocannabinoid can be cannabidiol. For example, the phytocannabinoid can be a combination of β-caryophyllene and cannabidiol.

In another embodiment of the present disclosure, the synthetic cannabinoid is HU-433, HU-308, a modified CBD (such as CBD-DMH) or combinations thereof. For example, the synthetic cannabinoid can be HU-433. For example, the synthetic cannabinoid can be HU-308. For example, the synthetic cannabinoid can be a modified CBD such as CBD-DMH or another synthetic cannabinoid that is a modified CBD with comparable activity to CBD-DMH. In an embodiment, the modified CBD is CBD-DMH. In another embodiment, the synthetic cannabinoid is a combination of HU-433, HU-308 and/or a modified CBD, optionally CBD-DMH.

In an embodiment, the ocular pharmaceutical composition comprises CBD-DMH. In another embodiment, the composition comprises at least one further CB2 target agent (e.g. HU 433, HU 308, β-caryophyllene, CBD or combinations thereof). In a further embodiment, the composition further comprises at least one further cannabimimetic agent (e.g. a non-selective cannabinoid receptor agonist such as $\Delta^8$-THC or a prodrug thereof, $\Delta^9$-THC or a prodrug thereof, CP 55,940, WIN 55,212-2 or combinations thereof).

It will be appreciated by a person skilled in the art that in the embodiments of the compositions of the present disclosure, the CB2 target agent and the cannabimimetic agent can also be varied as discussed herein for the embodiments of the methods and uses of the present disclosure.

The selection of a carrier suitable for ocular administration to an eye can be made by a person skilled in the art.

For example, phytocannabinoids, including THC and CBD, are typically poorly water-soluble, amorphous, highly viscous, and unstable in acidic solutions and when exposed to heat, air and light (Thumma, Majumdar et al. 2008). Beta-C and CBD-DMH also share most of these characteristics. Despite these properties, THC and CBD as well as other cannabinoids have been formulated for systemic administration, but with poor oral bioavailability. The inventors provide herein formulations for compounds such as Beta-C, CBD, CBD-DMH and HU-433 that can, for example act locally with minimal or no systemic effect. For example, the ocular pharmaceutical compositions of the present disclosure may be suitable for ocular topical, peri-ocular or intravitreal administration to an eye.

Biopharmaceutical characterization of these ocular drug delivery systems shows the extent of, e.g. Beta-C, CBD, CBD-DMH and HU-433 absorption following application. Plasma samples are collected and analyzed using the validated LC/MS assay methods to determine the ocular pharmacokinetics and distribution in multiple species (including rabbits and pigs). In addition, in vitro ocular permeability (www.absorption.com/ocular) and the potential ocular irritation of the chemicals and excipient used are determined using the Draize rabbit eye test (Draize, Woodard et al.

1944); the standard method for evaluating the ocular irritation/corrosion potential of a substance for regulatory purposes.

The eye presents a unique opportunity for localized direct drug delivery including corneal and transscleral delivery (periocular) of phytocannabinoid-based drugs, such as CBD, modified CBDs (e.g. CBD-DMH) and combinations thereof (e.g. CBD+Beta-C).

In anterior segment painful and/or inflammatory eye diseases such as uveitis and corneal neuropathic pain, drugs can be applied in various vehicles (emulsions, gels, liquid drops, etc.) to the cornea as ocular formulations or introduced via the periocular route from a conjunctival drug or posterior juxtascleral depot to reach anterior segment tissue structures and aqueous humor, and posterior structures (retina, optic nerve, retinal pigment epithelium, choroid and vitreous), respectively (Conway, 2008).

Liposomal encapsulation of cannabinoids and other compounds described herein can, for example enhance bioavailability and ocular efficacy compared to systemic drug injection. For example, non-psychotropic phytocannabinoid therapies suitable for ocular surface contact and periocular (transscleral) application in inflammatory ocular disease provide, for example a useful immunomodulatory therapy with fewer side effects than currently utilized immunosuppressive agents.

Liposomal formulations are established, safe and efficacious drug carriers for the delivery of poorly soluble lipophilic drugs (Agarwal et al., 2014). For example, they have been used in the formulation of drugs for controlled extended delivery with resultant increases in clinical efficacy in comparison to drug alone. For example, liposomes have been used to deliver a phytocannabinoid (see, for example: Sczcesniak et al., 2006).

It will be appreciated by a person skilled in the art that liposome formulations that are useful for delivery of a phytocannabinoid such as $\Delta^9$-THC may also be useful for delivery of other compounds such as the cannabinoids and other compounds described herein of the ocular pharmaceutical compositions of the present disclosure.

Accordingly, in an embodiment, the carrier suitable for ocular administration to an eye comprises a liposome.

Optionally, lipid components in the liposome formulations are phospholipids and cholesterol; excipients are tocopherol, antioxidants, viscosity-inducing agents and/or preservatives. The selection of suitable components can be made by a person skilled in the art.

For example, the phospholipids can be phosphatidylcholines, lysophosphatidylcholines, phosphatidylserines, phosphatidylethanolamines, phosphatidyl-glycerols, phosphatidylinositols or combinations thereof. Optionally, the phospholipid comprises, consists essentially of or consists of dipalmitoylphosphatidylcholine. Optionally, the phospholipids are provided in admixtures with modifying agents selected from the group consisting of cholesterol, stearyl amines, stearic acid, and tocopherols.

In an embodiment, the phospholipid and cholesterol are present in a molar ratio of from 20:1 to 1:1. In another embodiment, the phospholipid and cholesterol are present in a molar ratio of from 10:1 to 5:4. In a further embodiment, the phospholipid and cholesterol are present in a molar ratio of from 9:1 to 6:4. Optionally, the phospholipid and cholesterol are present in a molar ratio of 9:1 or 7:3 or 6:4. For example, the phospholipid and cholesterol are present in a molar ratio of 9:1. For example, the phospholipid and cholesterol are present in a molar ratio of 7:3. For example, the phospholipid and cholesterol are present in a molar ratio of 6:4.

In an embodiment, the ocular pharmaceutical composition contains the CB2 target agent and/or the cannabimimetic agent in an amount of from 0.01% to 10% by weight, based on the weight of the total composition.

Using a combined delivery platform with cyclodextrin complexation and liposomal incorporation can avoid the use of organic solvents to solubilize hydrophobic compounds and enables entrapment of the lipophilic phytocannabinoid complex into the aqueous core of liposomes. This approach therefore may not only increase drug solubility and stability but may also bypass the accelerated drug release that can occur following the more usual incorporation of hydrophobic drug into the liposomal lipid component (Maestrelli et al., 2010; 2005). Accordingly, the ocular pharmaceutical compositions of the present disclosure, for example those comprising CBD, modified CBD (e.g. CBD-DMH) and CBD or CBD-DMH combinations may also be delivered using drug-in cyclodextrin liposomal formulations. For example, a combined formulation approach of cyclodextrin complexation and entrapment in liposomes may be used to deliver ocular formulations of CBD or CBD-DMH and CBD-DMH or CBD-DMH combinations. Alternatively, use of the "double-loaded technique" can be exploited to load drug-cyclodextrin into the aqueous core of liposomes and drug alone into the lipid phase of liposomes providing, for example, a fast onset and an extended duration of action (Maestrelli et al., 2010). Another advantage associated with the use of cyclodextrin in the liposomal formulation for phytocannabinoid delivery may be that cyclodextrin complexation can improve drug permeation for ocular routes (Loftsson & Duchene, 2007; Loftsson & Stefansson, 2002). Accordingly, optionally, the carrier suitable for ocular administration to an eye comprises a cyclodextrin liposome.

In certain in vivo studies of the present disclosure, an oil-in-water emulsion was used to deliver phytocannabinoids and cannabinoids to the eye. Such emulsions comprised soya bean oil in either a viscous (>20% oil) or less viscous (<20% oil) formulation. A block co-polymer surfactant (Pluronic™ 668) was also used in some of the tested formulations.

Accordingly, in another embodiment, the carrier suitable for ocular administration to an eye comprises an oil-in-water emulsion formulation.

For example, the oily phase of the oil-in-water emulsion formulation comprises an oil, which may be a vegetable oil such as but not limited to soya bean oil. In an embodiment, the oil comprises, consists essentially of or consists of soya bean oil. Optionally, the oil comprises one or more medium chain triglyceride (MCT) oils (i.e. a triglyceride oil in which the carbohydrate chain has 8-12 carbons) or combinations of an MCT oil and a vegetable oil. MCT oils are available commercially. Examples of such MCT oils include TCR (trade name of Societe Industrielle des Oleagineaux, France for a mixture of triglycerides wherein about 95% of the fatty acid chains have 8 or 10 carbons) and MIGLYOL™ 812 (a mixed triester of glycerine and of caprylic and capric acids).

The oil-in-water emulsion formulations of the present disclosure also comprise an emulsifier. Suitable emulsifiers include a phospholipid or a mixture of phospholipids. For example, purified egg yolk phospholipids, soybean oil phospholipids or other purified phospholipid mixtures may be useful emulsifiers.

Additionally, the oil-in-water emulsion formulations of the present disclosure include a surfactant. For example, the surfactant can be a non-ionic alkylene oxide condensate of an organic compound which contains one or more hydroxyl groups. Suitable surfactants include, but are not limited to TYLOXAPOL™, compounds sold under the trade name TWEEN™, and PLURONIC™ F-68 (a copolymer of polyoxyethylene and polyoxypropylene). The TYLOXAPOL and TWEEN surfactants are FDA approved for human use.

The aqueous component of the oil-and-water emulsion formulations of the present disclosure is the continuous phase of the emulsion and may be water, saline or any other suitable aqueous solution which can, for example, yield an isotonic and pH controlled preparation.

The oil-in-water emulsion formulations of the present disclosure, for example used in the ocular pharmaceutical compositions of cannabinoids may comprise from 0.5 to 50% oil, from 0.1 to 10% emulsifier and from 0.05 to 5% surfactant. Optionally, in order to obtain a non-viscous composition, the concentration of the non-aqueous phase should generally not exceed 25%. For more viscous formulations this concentration is increased. The agent is optionally present in an amount of 0.05 to 5% by weight of the composition.

Both corneal and transscleral drug delivery in the eye can, for example, avoid the complications associated with invasive intraocular injections and also take advantage of the relatively high permeability of sclera structures to macromolecules (Hughes et al., 2005; Lobo et al., 2012; Ranta & Urtti, 2006). Additionally, use of viscous solutions or nanoparticles and liposomes has been effectively utilized via both corneal and transscleral routes to obtain sustain drug delivery in ocular structures for up to 2 weeks (Conway, 2008; Souto et al., 2010; Natarajan et al., 2012).

The inventors show that synergistic combination therapies with other *cannabis* constituents, for example those that act at CB2 receptors can produce anti-inflammatory and analgesic effects.

Another embodiment of the invention relates to formulations containing HU-433, a potent CB2 analog, CBD-DMH a potent CBD derivative and/or other modified CBDs. Products designed to treat neuropathic pain and uveitis are usefully provided as with the other embodiments discussed herein. These cannabinoid agents such as HU-433 and CBD-DMH can provide useful CB2 action, for example, for treatment of ocular neuropathic pain and uveitis.

Accordingly, the disclosure provides an ocular formulation of cannabinoids (e.g. Beta-caryophyllene [also referred to herein as Beta-C or βc], Cannabidiol [CBD], cannabidiol-dimethylheptyl [CBD-DMH] or other modified CBDs, HU-308 and HU-433, individually or in combinations of two or more of the foregoing) for treatment of ocular diseases.

The disclosure also includes an ocular pharmaceutical composition comprising a CB2 target agent, a cannabimimetic agent (such as a non-psychotropic cannabimimetic agent) or a combination thereof and a carrier suitable for ocular administration to an eye of the present disclosure for use for the ocular treatment of ocular inflammation and/or ocular neuropathic pain in a subject. It will be appreciated that the embodiments for such ocular pharmaceutical compositions for use can be varied as discussed herein for the ocular pharmaceutical compositions of the present disclosure and the methods and uses of the present disclosure, as appropriate.

For example, in an embodiment, the disclosure provides a phytocannabinoid formulation (e.g. CBD derivatives, or a combination of CBD+R-caryophyllene) for administration to the cornea and/or other ocular depots for treatment of eye diseases causing inflammation in a subject, such as intraocular (uveitis) or extraocular (corneal neuropathic hyperalgesia).

Combination ocular therapies of CBD or CBD derivatives with agents such as β-caryophyllene, a $CB_2$ agonist, can enhance the efficacy of CBD in the treatment of inflammatory and/or neuropathic eye disease.

III. Methods and Uses

Without being bound by theory, cannabimimetics, optionally cannabimimetics that target CB2 such as phytocannabinoids that target CB2 (for example, CBD which is a CB2 partial agonist) and synthetic cannabinoids that target CB2 (for example, modified CBDs such as CBD-DMH which is a CB2 positive allosteric modulator) may, for example be effective in reducing markers of inflammation. For example, such compounds may reduce pro-inflammatory cytokine signaling, oxidative stress and/or inhibit activated immune cells (microglia); all of which are also features of tissue damage seen in experimental models of acute and chronic ocular inflammation, and which are exacerbated in animals lacking CB2 receptors.

The anti-inflammatory and immunomodulatory ocular effects of CBD in experimental models were achieved with doses of 5-10 mg/kg of CBD, which is comparable to that of therapeutic doses utilized in humans to alleviate neuropathic pain and spasticity associated with multiple sclerosis (Oreja-Guevara, 2012a,b). The inventors provide the first studies specifically addressing the use of CBD for ocular inflammation and pain.

There is a substantive therapeutic window for efficacy and excellent tolerability, respectively, for the phytocannabinoid, CBD, in the treatment of inflammatory eye diseases. Without being bound by theory, CBD appears to exert its actions via modulation of the endocannabinoid system as well as non-endocannabinoid system targets that can collectively modulate cellular signaling pathways involved in inflammation and pain. CBD is not psychotropic and its versatile pharmacology underscores its usefulness for combinations with other anti-inflammatory and immunomodulatory agents, including the terpenoid, β-caryophyllene, which acts at CB2. These pharmacological properties of CBD therefore can, for example provide useful combination phyto-therapeutic products (i.e. CBD and/or CBD derivatives (also referred to herein as modified CBDs)+β-caryophyllene) for enhanced actions. The delivery platform of this formulation is optionally based on liposomal formulations, optimized for the eye.

The invention provides the first disclosure of R-caryophyllene for use in the eye in humans. β-caryophyllene is useful, for example, for combination therapy with CBD for ocular inflammatory and neuropathic disease. An additional advantage can, for example be that the physicochemical properties of R-caryophyllene are similar to CBD such that both of these compounds are readily delivered together using the proposed drug, for example in cyclodextrin or liposome preparations.

The inventors demonstrate herein the anti-inflammatory and analgesic properties of novel ocular formulations such as those comprising CBD and other cannabinoids in experimental models of ocular inflammatory disease. The disclosure thus provides, for example, methods of treatment of inflammation by administering cannabinoids to the eye of a subject.

Experimental models of uveitis and corneal hyperalgesia are used to show the local delivery of CBD formulations (e.g. CBD, combination CBD+β-caryophyllene) and cannabinoids (CBD-DMH, HU-308, HU-433) for the treatment of ocular inflammation and pain. These models are established and the inventors have considerable experience with their use for pharmacological studies of various agents, including cannabinoids, as well as preclinical studies of ocular cannabinoid drug delivery and tolerability.

Accordingly, the present disclosure includes a method of treating ocular inflammation and/or ocular neuropathic pain in a subject in need thereof, comprising administering ocularly to the subject in need thereof a CB2 target agent, a cannabimimetic agent or a combination thereof. Optionally, the method is a method of treating ocular inflammation. In another embodiment, the method is a method of treating ocular neuropathic pain. In a further embodiment, the method is a method of treating ocular inflammation and ocular neuropathic pain.

The present disclosure also includes an ocular use of a CB2 target agent, a cannabimimetic agent or a combination thereof for treatment of ocular inflammation and/or ocular neuropathic pain in a subject in need thereof. Optionally, the use is for treatment of ocular inflammation. In another embodiment, the use is for treatment of ocular neuropathic pain. In a further embodiment, the use is for treatment of ocular inflammation and ocular neuropathic pain.

The present disclosure further includes a use of a CB2 target agent, a cannabimimetic agent or a combination thereof for preparation of an ocular medicament for treatment of ocular inflammation and/or ocular neuropathic pain in a subject in need thereof. Optionally, the use is for preparation of a medicament for treatment of ocular inflammation. In another embodiment, the use is for preparation of a medicament for treatment of ocular neuropathic pain. In a further embodiment, the use is for preparation of a medicament for treatment of ocular inflammation and ocular neuropathic pain.

In an embodiment, the CB2 target agent comprises, consists essentially of or consists of a CB2 agonist agent, a CB2 partial agonist agent, a CB2 positive allosteric modulator or a combination thereof. In another embodiment, the CB2 target agent is a CB2 positive allosteric modulator.

As CBD-DMH is a positive allosteric modulator (PAM) of G protein mediated signaling at $CB_2$ receptors and testing will show that CBD-DMH is a partial agonist/positive allosteric modulator (ago-PAM) at $CB_1$, benefit would be expected in terms of reducing both pain and inflammation, preventing corneal hypersensitivity (neuropathic pain) and enhancing wound healing. Furthermore, as CBD-DMH can act as an allosteric modulator at $CB_2$ receptors and testing will show that CBD-DMH can act as an allosteric modulator at $CB_1$ receptors, CBD-DMH can also promote the actions of orthosteric ligands that can act at either or both of these receptors including: non-selective cannabinoids such as THC, WIN 55,212-2 and CP 55,940, and selective $CB_2$ agonists including HU 308 and HU 433. Thus, combinations of CBD-DMH and a non-selective cannabinoid or either a $CB_1$ or $CB_2$ agonist may result in useful therapeutic efficacy at lower doses of either or both cannabinoids. Additionally, as both $CB_2$ and $CB_1$ receptors have been reported to be upregulated following trauma or in disease, the allosteric/agonist actions of CBD-DMH alone at cannabinoid receptors would enhance endocannabinoid signaling and therefore therapeutic benefit. Accordingly, in an embodiment, the CB2 target agent is CBD-DMH.

For intraocular inflammation such as uveitis (including anterior, posterior and pan-uveitis), non-selective cannabinoids (i.e. acting at CB1/CB2) and CB2 selective agents can reduce inflammation. In anterior uveitis (i.e. iritis), and extraocular inflammation such as episcleritis and scleritis, the relief of inflammation also relieves associated pain. In these conditions, CB2 receptor activation is more useful than CB1 receptor activation for reducing inflammation and immune cell activation and recruitment. Accordingly, for intraocular inflammation (e.g. uveitis), use of CB2 target agent alone is useful to prevent inflammation and relieve symptoms. A CB2 positive allosteric modulator such as CBD-DMH in combination with a CB2 target agent may, for example, result in a lower dose needed for the CB2 target agent. This may, for example, lead to less chance of tolerance, for example, with long-term treatment.

Accordingly, in another embodiment, the method comprises administering a CB2 positive allosteric modulator (such as CBD-DMH) in combination with at least one further CB2 target agent. In another embodiment, the at least one further CB2 target agent is HU 433, HU 308, β-caryophyllene, CBD or combinations thereof. In a further embodiment, the at least one further CB2 target agent is HU 433 or HU 308. It is an embodiment that the at least one further CB2 target agent is HU 433. In another embodiment, the at least one further CB2 target agent is HU 308. In an embodiment, the dosage of the CB2 positive allosteric modulator (e.g. CBD-DMH) and/or the at least one further CB2 target agent is less than the dosage of such agents when used alone.

In another embodiment, the method comprises administering the CBD-DMH in combination with at least one further cannabimimetic agent. In an embodiment, the dosage of the CBD-DMH and/or the at least one further cannabimimetic agent is less than the dosage of such agents when used alone.

In the case of corneal trauma resulting in pain and inflammation, activation of both CB1 and CB2 receptors may be used for optimal relief of pain and inflammation after injury allowing for enhanced wound healing (less scarring of corneal surface) and prevention of corneal hyperalgesia (neuropathic pain). Therefore, a non-selective cannabinoid and/or a CB1/CB2 allosteric modulator (e.g. CBD-DMH) could be used rather than a CB2 agonist.

Non-selective cannabinoids such as but not limited to THC, CP 55,940 and WIN 55,212-2 would be expected to be efficacious in reducing ocular inflammation and pain as they can activate both cannabinoid receptors. However, long term use of these orthosteric agents at therapeutic doses can, for example, produce tolerance and unwanted behavioral and other possible off-target side-effects (Pertwee, 2009, 2012, Davis, 2014). An allosteric modulator generally has no actions at the receptor in the absence of an orthosteric ligand. However, when the allosteric modulator is bound to the receptor it can enhance (positive allosteric modulator; PAM) or decrease (negative allosteric modulator) the actions of the orthosteric ligand. For a positive allosteric modulator, benefits may include: improved therapeutic index with use of lower doses of the orthosteric ligand. This would produce less receptor desensitization (tolerance) and less side-effects. Furthermore, in the case of endogenous ("constitutive") receptor activity as is expected with upregulation of cannabinoid receptors after injury, an agent with PAM activity at cannabinoid receptors would produce localized enhancement of the beneficial actions of endocannabinoid signaling at the tissue site of injury.

CBD-DMH is a PAM at CB2 and testing will show that CBD-DMH is an ago-PAM at CB1 (produces PAM actions at lower doses and weak CB1 agonist actions at higher). Therefore it can enhance non-selective orthosteric ligands that act at these receptors. As CB2 receptors (while not wishing to be limited by theory, also CB1) are significantly upregulated in ocular inflammation (Toguri et al., 2014), CBD-DMH can therefore promote the actions of endocannabinoids acting at both cannabinoid receptors. In case of corneal injury and corneal neuropathic pain, a mixed CB1/CB2 target agent may, for example, provide for additional benefits including analgesia and enhanced wound healing (CB1; CB1 receptors are highly expressed in corneal epithelial cells; Straiker et al., 1999; Yang, 2013) and reduction in corneal inflammation and neuropathic pain (CB1 and CB2).

Accordingly, in another embodiment, the method comprises administering the CBD-DMH in combination with at least one further cannabimimetic agent that is a non-selective cannabinoid receptor agonist. In a further embodiment, the non-selective cannabinoid receptor agonist is selected from $\Delta^8$-THC or a prodrug thereof, $\Delta^9$-THC or a prodrug thereof, CP 55,940, WIN 55,212-2 and combinations thereof. In another embodiment, the non-selective cannabinoid receptor agonist is $\Delta^8$-THC or a prodrug thereof. In a further embodiment, the non-selective cannabinoid receptor agonist is $\Delta^9$-THC. It is an embodiment that the non-selective cannabinoid receptor agonist is CP 55,940. In another embodiment, the non-selective cannabinoid receptor agonist is WIN 55,212-2. The selection of a suitable non-selective cannabinoid receptor agonist can be made by the person skilled in the art. In an embodiment, the dosage of the CBD-DMH and/or the at least one further cannabimimetic agent that is a non-selective cannabinoid receptor agonist is less than the dosage of such agents when used alone.

Both $\Delta^9$-THC and $\Delta^8$-THC can activate CB1 and CB2 receptors. The actions of THC are described as partial agonist in most tissues depending on the co-existing concentrations of endocannabinoids and/or other orthosteric full agonists. For example, a partial agonist may act on its own as an agonist but, in the presence of a full agonist, it may act to decrease the efficacy of the full agonist hence in this latter situation it can act as an antagonist.

It will be appreciated by a person skilled in the art that in embodiments of the methods and uses of the present disclosure, the CB2 target agent and the cannabimimetic agent (such as a non-psychotropic cannabimimetic agent) can also be varied as discussed herein for the embodiments of the compositions of the present disclosure.

In an embodiment, the method is a method of treating ocular inflammation, optionally ocular inflammation which is not associated with ocular neuropathic pain. In another embodiment, the method is a method of treating ocular inflammation caused by a non-infectious condition.

Posterior uveitis is not clinically associated with pain. Generally conditions with moderate or mild chronic inflammation in the retina do not present with pain but can result in loss of retinal neurons and vision loss. Accordingly, in an embodiment, the method is a method of treating inflammation which does not present with pain, for example a condition selected from posterior uveitis, retinitis, uveoretinitis and proliferative vitreoretinopathy.

Alternatively, it will be appreciated by a person skilled in the art that some conditions associated with ocular inflammation further present with pain that is not neuropathic pain and that treating of the inflammation will reduce the pain. Accordingly, in another embodiment, the ocular inflammation further presents with non-neuropathic pain and the treatment reduces the pain. In an embodiment, the condition is selected from anterior uveitis, episcleritis and scleritis.

Iritis (anterior uveitis) can be caused by infectious and non-infectious conditions. In an embodiment, the condition is a non-infectious condition. Uveitis can also be idiopathic. Further, blunt trauma to the eye can cause traumatic inflammation of the iris. Non-traumatic iritis is frequently associated with certain diseases, such as ankylosing spondylitis, Reiter syndrome, sarcoidosis, inflammatory bowel disease, and psoriasis.

Corneal inflammation can lead to corneal neuropathic pain (hyperalgesia). Corneal neuropathic pain can result from an initial trauma and inflammatory response, or as a result of persistent chronic inflammation/irritation (i.e. dry eye condition). Most frequently described ocular neuropathic pain conditions are associated with corneal injury and inflammation; inflammation is a significant contributor to neuropathic pain syndromes (Guindon and Hohmann, 2008). Corneal neuropathic pain typically presents with allodynia (abnormal response to normal stimuli) and hyperalgesia (exaggerated response to mild noxious stimuli). Corneal pain conditions are very common as the cornea is highly innervated with sensory nerves. Accordingly, in an embodiment, the method is a method for treating ocular inflammation and neuropathic pain caused by a non-infectious condition. In an embodiment, the ocular neuropathic pain is corneal neuropathic pain. In an embodiment, the ocular neuropathic pain arises from dry eye, trauma (e.g. refractive surgery), a corneal abrasion, a corneal burn, a corneal transplant, an autoimmune disease or an allergen. It will be appreciated by a person skilled in the art that such conditions typically present with both neuropathic pain and inflammation and that treatment with methods of the present application can reduce the ocular inflammation and hence the ocular neuropathic pain. Other treatments such as use of a local anesthetic may be used to reduce pain in such conditions but this would not reduce the ocular inflammation. It will be appreciated by a person skilled in the art that corneal neuropathic pain can also arise from infection (e.g. viral or bacterial).

In another embodiment, the ocular inflammation is caused by the subject having an eye disease.

In an embodiment, the eye disease causes intraocular inflammation. Optionally, the eye disease is uveitis, uveoretinitis or proliferative vitreoretinopathy.

In another embodiment of the present disclosure, the eye disease causes extraocular inflammation. Optionally, the eye disease is corneal inflammation or neuropathology, episcleritis or scleritis.

In another embodiment, the eye disease causes pain and loss of vision, and the agent reduces the pain and/or reduces the loss of vision.

The dosage of the CB2 target agent and/or the cannabimimetic agent (such as the non-psychotropic cannabimimetic agent) can vary depending on many factors such as the pharmacodynamic properties of these compounds, the mode of administration, the age, health and weight of the subject, the nature and extent of the ocular inflammation or ocular neuropathic pain, the frequency of the treatment, the type of concurrent treatment, if any, the clearance rate of the compound in the subject to be treated and whether the CB2 target agent and/or the cannabimimetic agent is administered alone or in combination with, for e.g., a CB2 positive allosteric modulator such as CBD-DMH. One of skill in the art can determine the appropriate dosage based on the above factors. For example, the CB2 target agent and/or the cannabimimetic agent such as a phytocannabinoid (e.g. CBD, CBD+ β-caryophyllene) and synthetic cannabinoid-containing ocular formulations (e.g. HU-433, HU-308, CBD-DMH) can be delivered via the cornea and transscleral routes (periocular) at various doses, optionally 0.1-10% w/v.

Dosing regimens include single dose treatments as well as multiple dosing. The CB2 target agent and/or the cannabimimetic agent may be administered initially in a suitable dosage that may be adjusted as required, depending on the clinical response.

Optionally, the agent is administered topically to the eye; i.e. the agent is for ocular topical use. In another embodiment, the agent is administered intravitreally to the eye; i.e. the agent is for intravitreal use. In a further embodiment of the present disclosure, the agent is administered periocularly to the eye; i.e. the agent is for periocular use.

The following non-limiting examples are illustrative of the present disclosure:

EXAMPLES

Certain data has been generated using several different animal models as explained in the methods sections. These can be divided into ocular inflammation models and ocular neuropathic pain models.

Example 1

Effects of the CB2 Receptor Agonist, HU-433 on Endotoxin-Induced Uveitis

I. Purpose

This study showed the anti-inflammatory role of the cannabinoid 2 receptor (CB2R) agonist, HU-433 on intraocular inflammation in an endotoxin-induced uveitis (EIU) model in rats.

II. Introduction

Tissue histology and immunohistochemistry: Ocular inflammation is accompanied by tissue edema, migration of immune cells to the sites of injury and pathology. Histology allows the tissue structure to be accessed for edema and structural dissolution, along with evidence of plasma extravasation (indicative of pathological changes in microvascular structure). Use of antibodies to proteins expressed by immune cells including neutrophils, macrophages and microglia, allows identification of immune cell types recruited to sites of tissue damage in the anterior and posterior ocular tissues.

Intravital imaging for real-time quantitative measurement of leukocyte adhesion and migration: Tissue damage or injury results in alterations in capillary blood flow and microvascular structure, as well as adhesion and transmigration of immune cells (leukocytes) from the blood vessel to accumulate at the site of tissue injury (inflammation). This is a necessary host response to resolve injury, however escalation of the inflammatory response or persistent inflammatory responses can lead to tissue damage (Ley, Laudanna et al. 2007). Quantification of leukocytes adhering to the cells lining the lumen of blood vessels (endothelium) is carried out dynamically in the iridial microvasculature using intravital microscopy to directly visualize in real-time, or histologically in the post-mortem retina, leukocyte adhesion and diapedesis.

Assessment of pro-inflammatory markers (cytokines, adhesion molecules): The levels of adhesion molecules and pro-inflammatory mediators (cytokines) are analyzed by immunoassay of respective protein levels to provide assessment of immune status.

Approaches such as tissue histology/pathology, IVM and cytokine analysis provide a measure of the inflammatory response. Immunomodulatory and anti-inflammatory drugs reduce leukocyte adhesion and pro-inflammatory markers and tissue damage and promote inflammation resolution (Sanz and Kubes 2012).

III. Materials and Methods

The endotoxin-induced uveitis (EIU) model is a widely used animal model of human bacterially-derived uveitis, involving inflammation of the uveal tract. The uveal tract comprises the middle layer of the eye, including the iris, ciliary body and uvea.

EIU was induced in male Lewis rats by intravitreal injection of 100 ng of lipopolysaccharide (LPS, *Escherichia coli*) in saline. Treatments of the cannabinoid 2 receptor (CB2R) agonist, HU-433 were administered, in the presence and absence of the selective antagonist, AM630. Cannabinoid treatments involved intravenous (i.v.) HU-433 (0.001-1 mg/kg), AM630 (2.5 mg/kg i.v.) and AM630+HU-433, administered 15 minutes after intravitreal injection of LPS. Intravital microscopy (IVM) was used to observe leukocyte-endothelial adhesion each hour after induction of EIU for a duration of 6 hours.

IV. Results and Discussion

Figure 1:
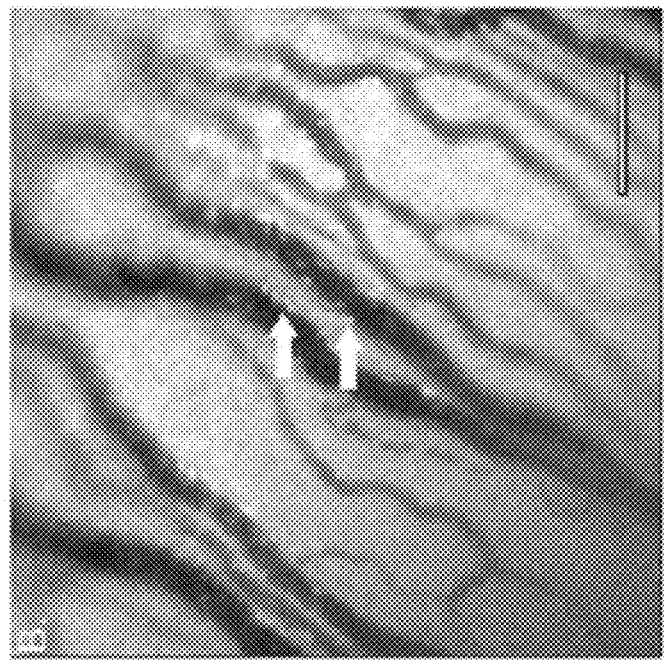
FIG. 1 shows representative intravital microscopy (IVM) images of iridial microcirculation in rat eye showing adherent leukocytes at 6 hours after intravitreal injection of: (A) saline, and (B) lipopolysaccharide (LPS). Scale Bar=100 μm. Arrows indicate adherent leukocytes.
Figure 1:
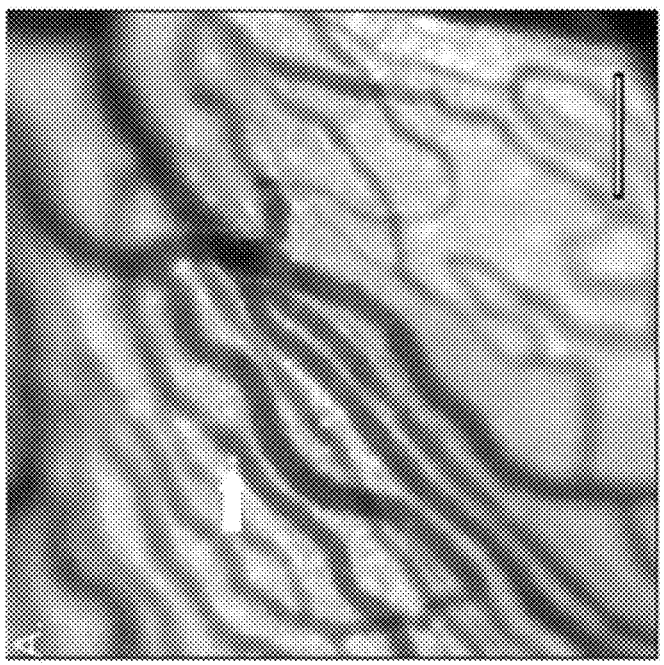

Data in FIG. 1 was collected from experiments using an animal model of ocular inflammation called endotoxin-induced uveitis. This model has been shown to cause inflammation within the eye. The level of inflammation is quantified by counting the number of adherent leukocytes in the iris microcirculation. Leukocytes must adhere to the microvasculature for more than 30 s (measured as adherent leukocytes per $mm^2$). Imaging was conducted in a minimum of 4 quadrants within the eye, 4 vessels each quadrant, 6 hours after inflammation was induced.

FIG. 1A is a representative image of the iris microcirculation after an injection of saline into the eye (control); leukocytes are the white dots within the black vasculature. FIG. 1B is a representative image of the iris microcirculation after injection of lipopolysaccharide (LPS) into the eye. LPS is an inflammatory agent derived from gram-negative bacteria. LPS causes a significant increase in the number of leukocytes adhering to the vasculature compared to the saline injection.

HU-433 at doses of 0.01 and 0.1 mg/kg (FIGS. 2-4) significantly ($p<0.01$) reduced leukocyte-endothelial adhesion (inflammation) 6 hours after induction of EIU. This decrease in leukocyte adhesion was abolished when animals were treated with the CB2R antagonist AM630 prior to treatment with HU-308 in EIU. Use of the CB2R antagonist alone caused a significant increase in the number of adherent leukocytes to the microvasculature ($p<0.01$).

FIG. 2A is a representative image of inflammation within the iris which can be compared to after treatment with HU-433 (FIG. 2B).

Figure 3:
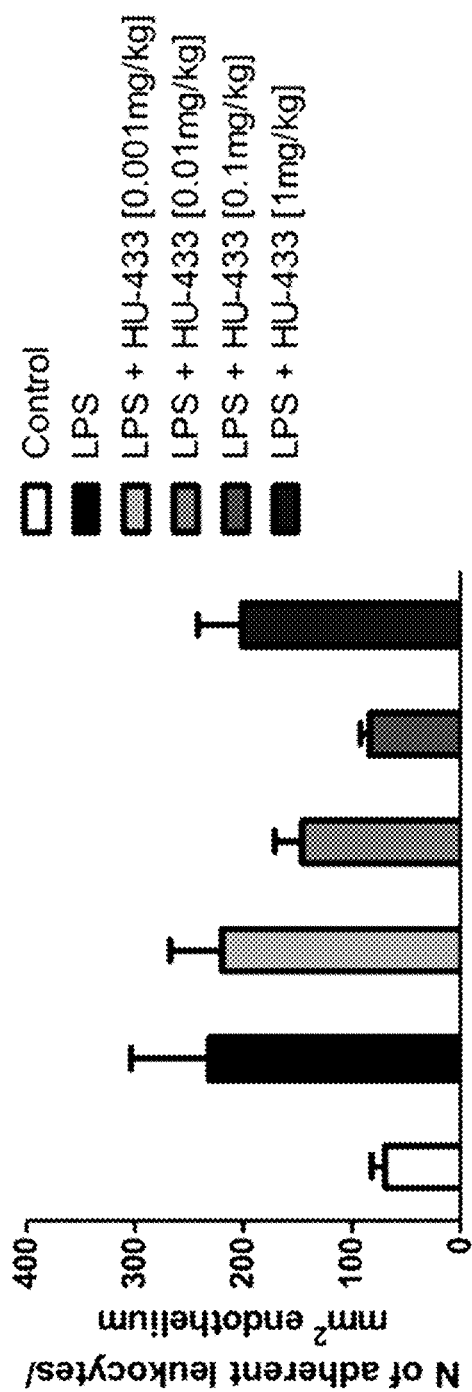
FIG. 3 is a bar graph of dose-response for i.v. administration (0.001-1 mg/kg) of cannabinoid, HU-433, on leukocyte adhesion in iridial venules in control and LPS-treated animals (n=3-7 per group). Values are represented as number of adherent leucocytes/mm$^2$ endothelium and are shown as mean+SEM. $P<0.01$ for an HU-433 dose of 0.1 mg/kg.
Figure 4:
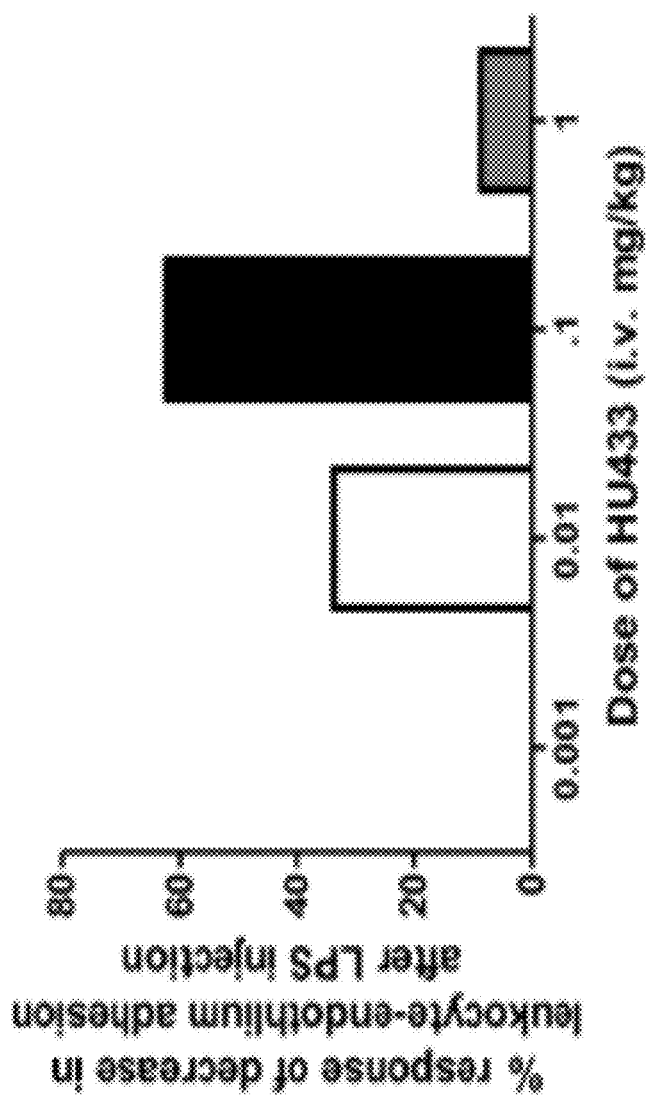
FIG. 4 is a bar graph showing the average percent decrease in leukocyte-endothelium adhesion after intravitreal LPS injection in the presence of various doses of the cannabinoid, HU-433, given i.v. at doses of 0.01-1 mg/kg compared to LPS treatment alone (n=3-7 per group). Values represent means.

FIG. 3 is the dose response curve of HU-433 used to treat ocular inflammation in the present study. It was demonstrated (FIG. 3) that HU-433 (0.1 mg/kg) was able to significantly ($p<0.05$) reduce the number of adherent leukocytes in the iris microcirculation. This data is also depicted as the average decrease of adherent leukocytes compared to LPS alone with different doses of HU-433 (FIG. 4).

CB2R activation by using the cannabinoid, HU-433 reduces leukocyte recruitment to the iris and decreases local release of inflammatory mediators during acute EIU. Drugs targeting the CB2R are useful as therapeutics for uveitis and decreasing acute ocular inflammation.

Example 2

Effects of Administration of the Synthetic Cannabinoid, CBD-DMH on LPS Induced Uveitis I. Materials and Methods
Tested Compound:
CBD-DMH
Subjects:
Two different EIU experimental groups were examined in BALB/c Mice:
  Group (A): Intravital microscopy (IVM) at 5 hours after intravitreal injection of saline (control)
  Group (B): IVM at 5 hours after induction of EIU and i.v. administration of drug vehicle control (1 time, 0.2 mL 30% ethanol in saline right after intravitreal injection)
  Group (C): IVM at 5 hours after induction of EIU and i.v. administration of cannabinoid (1 time, 0.2 mL 10 mg/kg CBD-DMH right after intravitreal injection).
Intravitreal Injection of LPS to Induce Uveitis:
The strain of animals chosen for these experiments was based on preliminary testing conducted and published literature (see, for example: Toguri et al., 2014). The strain of mice chosen was BALB/c and Lewis rats were used. Animals were anesthetised prior to induction of uveitis. Mice were anesthetized with 5% isoflurane in 100% oxygen. Rats were anesthetized with 65 mg·kg$^{-1}$ of sodium pentobarbital. Depth of anesthesia was monitored via toe pinch test. The head of the animal was immobilized, and the sclera of the left eye was punctured with a 30-gauge needle at the dorsonasal quadrant at approximately the level of the equator. Mice received a total of 250 ng of LPS (*E. coli* 026:B6; Sigma-Aldrich, Oakville, ON, Canada) in 2 µl of sterile 0.9% saline. Rats received a total of 100 ng of LPS in 5 µl of sterile 0.9% saline. Intravitreal injections were made under microscopic control with a Hamilton syringe (Hamilton Company, Reno, Nev., USA), with a 30 G1/6 needle. To avoid touching the lens or causing any damage to the eye, the tip of the needle was directed towards the posterior pole and only the bevelled tip (2-3 mm) entered the vitreal cavity. The needle was held in place after injection for 5 seconds to avoid leakage of the LPS from the site of injection (sclerostomy). Sclerostomy was closed by tissue adhesive to prevent any leakage. Animals with bleeding or swelling post injection were excluded from the study.

In Vivo Imaging:
The technique of intravital microscopy (IVM) was used for in vivo investigation of leukocyte recruitment. The intravital fluorescence video microscope was focused on the iridial microcirculation, which allowed for imaging of the leukocyte-endothelial interactions. Throughout IVM, the animal's head was made stationary The iris was divided into four equal quadrants by drawing two superficial lines, lengthwise and widthwise. IVM was carried out at each of these quadrants. In each video, leukocyte recruitment was observed and recorded for 30 seconds each. Data analysis was conducted off-line.

IVM Analysis:
Several videos of each quadrant were recorded for 30 seconds. Leukocyte adhesion was the parameter analyzed. Adherent leukocytes was defined as the number of leukocytes during the 30 s observation period that did not detach from the cylindrical endothelial surface. The number of adherent leukocytes within each vessel segment was calculated by measuring the diameter and length of vessel segment studied, assuming a cylindrical geometry of blood vessel. Adherent leukocytes were expressed as number of cells per mm$^2$ of endothelial surface.

IVM Data Analysis:
Results were analyzed using the software Prism 5 (GraphPad Software, La Jolla, Calif., USA). All data are expressed as means±standard error mean (SEM). Groups were tested for significance using one-way analysis of variance (ANOVA) with a Dunnett's post hoc test, comparing all experimental groups to the vehicle treated group. Significance was considered at $p<0.05$.

Figure 5:
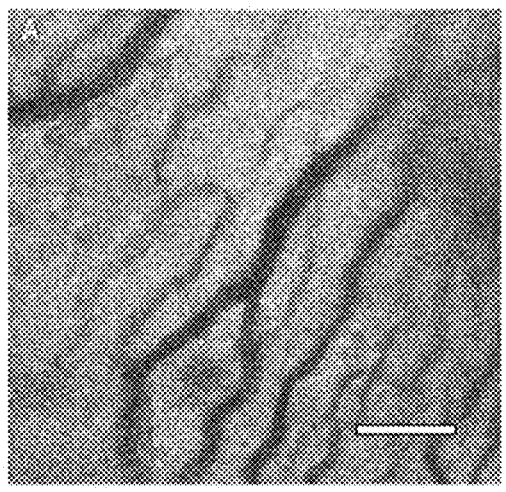
FIG. 5 shows representative still images of intravital microscopy of the iridial microcirculation in CD1 mice at 5 hours after intravitreal LPS injection in the following groups: (A) control (saline injection); (B) LPS injection+ vehicle control (Saline+DMSO); (C) LPS+the cannabinoid, CBD-DMH; and (D) an image of a control eye on lowest magnification showing iridal microvasculature. Arrows indicate adherent leukocytes. Scale Bar=100 μm.
Figure 5:
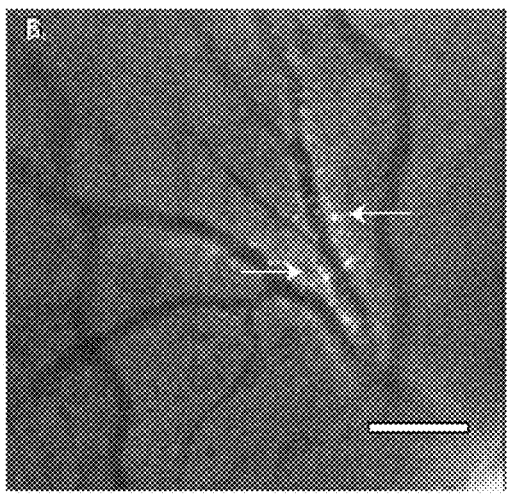
Figure 5:
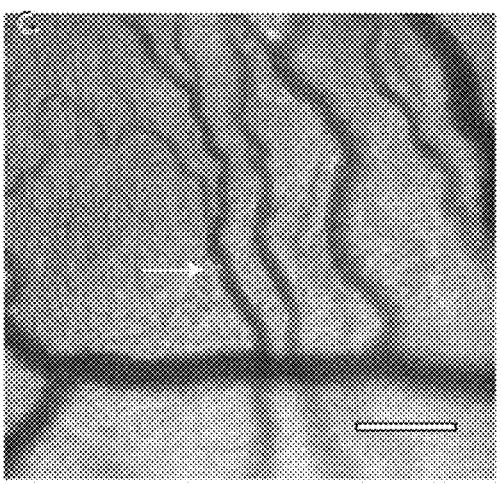
Figure 5:
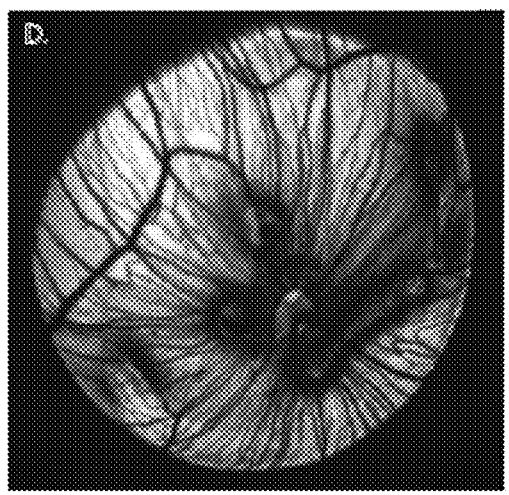
Figure 6:
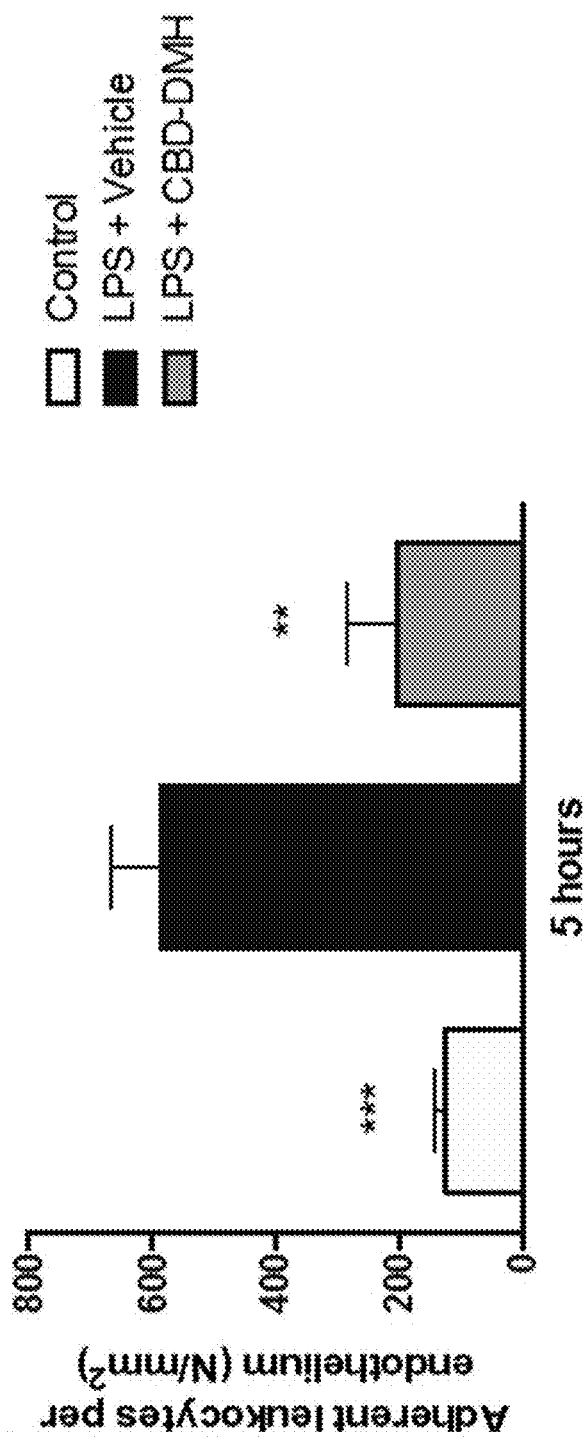
FIG. 6 depicts a bar graph of IVM measurements examining the mean number of adherent leukocytes for the groups in FIG. 5: Control (n=5), LPS+vehicle (n=4), LPS+CBD-DMH (n=4).  $P<0.01$ compared to the LPS+vehicle group. * $P<0.001$ compared to the LPS+vehicle group. Values represent mean±SEM.

II. Results and Discussion
FIG. 5 shows representative images of the microvasculature and adherent leukocytes: (A) saline injection; (B) LPS injection; and (C) a decrease in number of adherent leukocytes with CBD-DMH. Inflammation was quantified by measurement of adherent leukocytes to the endothelium 6 hours after LPS injection (FIG. 5D). FIG. 6 depicts a bar graph of IVM measurements examining the mean number of adherent leukocytes for the groups of FIG. 5.

Example 3

Effects of Administration of CBD-DMH, CBD or a Combination of CBD+βC on a PVR-Dispase Model of PVR I. Background
Following retinal detachment surgery or ocular trauma, 5-10% of patients may develop proliferative vitreoretinopathy (PVR) (Yanoof & Duker, 2009). There are currently no non-surgical treatments for PVR which can be classified in 3 main stages: an inflammatory stage with activation and migration of immune cells including neutrophils, macrophages and microglia, an early proliferative stage and a late proliferative stage. In the early inflammatory stage, the ocular trauma can cause retinal tears and folds and retinal detachment. Lack of resolution of the inflammation results in astrocyte proliferation and remodelling, epiretinal membrane formation and retinal detachment with resultant fibrosis.

Experimental PVR lesions can be generated using intravitreal injections of the proteolytic enzyme, dispase (3 µl of 0.1-0.3 U/µl dispase). This results in a chronic inflammatory response with the development of retinal tears and folds within 1-3 weeks post-injection (technique modified from Frenzel et al., 1998). The Dispase PVR model provides a useful model for chronic posterior ocular inflammation, astrogliosis and fibrosis.

II. Materials and Methods
Animals:
C57Blk/6 male mice (20-25 g; Charles Rivers, QC, Canada) were used for the experiments. The animals were housed on a 12 hrs light/dark cycle, with unrestricted access to food and water. All experiments were conducted in accordance with the standards and procedures of the Canadian Council on Animal Care and the Dalhousie University animal care committee.

Intravitreal Injections:
The PVR was induced in C57Blk/6 animals with an intraocular injection of dispase (Sigma), a neutral protease which cleaves basement membrane, into the dorso-lateral quadrant of the left eye. Dispase was diluted to the concentration of 0.2 U/µl in a sterile Ringer saline solution. Intraocular injections (2 µl) were made under a microscope with a Hamilton syringe attached to a 30 G needle. Control animals received 2 µl of sterile Ringer saline solution.

Drug Treatment:

Animals were treated with daily intraperitoneal injections of cannabinoid ligands: CBD-DMH (10 mg/kg), CBD (10 mg/kg) and CBD (10 mg/kg)+β-Caryophyllene (20 mg/kg), for a period of seven days. One week following the induction of PVR, mice were sacrificed by an i.p. overdose of sodium pentobarbital (250 mg/kg), eyes were inoculated and prepared for histological or immunohistochemical staining.

Clinical Scoring:

The external morphology of the eyes was evaluated by clinical scoring at 7 days following the intraocular injection. The severity of the PVR was determined on a scale of 0-5, with 0 (no disease) to 5 (completely degenerated eye) as detailed in Table 1.

TABLE 1

Clinical scoring for evaluation of experimental murine PVR

| Clinical Stage | Description |
| --- | --- |
| 0 | No clinical signs of the disease |
| 0.5 | Dilated iris vessels |
| 1 | Swollen blood vessels in the iris; sporadic abnormal miosis |
| 2 | Pupil partially covered with fibrin, hazy anterior chamber |
| 3 | Exudate in anterior chamber, but pupil still visible |
| 4 | Exudate with haemorrhage (opaque anterior chamber), completely obscured pupil |
| 5 | No exudate in anterior chamber, abnormal pupil configuration, degenerating iris |

The data was analyzed by One-Way ANOVA analysis, followed by Kruskal-Wall is test. $p<0.05$ was considered significant.

Histology:

The internal anatomy morphology of the eye was visualized by haematoxylin and eosin (H&E) staining. The severity of the disease was scored under the light microscope and was evaluated with the scoring system of 0 (no disease) to 4 (severely damaged ocular tissue) as detailed in Table 2.

TABLE 2

Histopathology scoring for experimental murine PVR

| Histopathology | Description |
| --- | --- |
| 0 | No disease, normal retinal architecture |
| 0.5 | Mild inflammatory cell infiltration in the retina, no tissue damage |
| 1 | Infiltration, retinal folds and focal retinal detachments, few small granulomas in choroid & retina |
| 2 | Mod. infiltration, retinal folds, detachment, focal photoreceptor damage, granulomas, perivaculitis |
| 3 | Moderate to marked infiltration, extensive photoreceptor damage. Exudate with hemorrhage (opaque anterior chamber), completely obscured pupil |
| 4 | Severe inflammation and/or full thickness retinal damage with serous exudates and subretinal neovascularisation, large granulomatous lesions |

Immunohistochemistry:

Eyes were inoculated and immersed in 4% (paraformaldehyde (PFA) in 0.1 M phosphate buffer for 24 hrs. Then the eyes were transferred into 30% sucrose in phosphate buffered saline (PBS) for cryoprotection. Symmetrical sagittal sections (14 μm) of the whole eye were cut on a freezing microtome and collected on the microscope slides. For immunohistochemical staining, slides were washed in PBS (3×15 min), and then were incubated for 1 hr at room temperature with 10% normal goat serum (Vector Labs). This step was followed by overnight incubation of sections, at 4° C., with the primary antibodies: anti-rabbit Iba1 (Wako Chemicals, CA; 1:100), anti-rabbit glial fibrillary acidic protein (GFAP; astrocyte marker) (Chemicon, Temecula, Calif. 1:1000). Fluorescent-tagged antibodies $CY^{TM3}$ goat anti-rabbit IgG (1:500, Jackson ImmunoResearch Laboratories) were used for visualization of Iba1 and GFAP. The microglia counts were performed under the fluorescence microscopy.

III. Results and Discussion

Proliferative vitreoretinopathy (PVR) is a model of ocular inflammation that occurs with both external and internal changes in the eye. This inflammation is caused by intraocular injection of dispase. Several different cannabinoid treatments were tested in this model. Inflammation was quantified by clinical scoring (FIG. 7A), histology (FIG. 7B) and immunohistochemistry (FIG. 7C). Clinical scoring, histology and immunohistochemistry are explained herein under the PVR method.

CBD-DMH significantly decreased the clinical scores and histological scores received in the model of PVR indicating its ability to reduce ocular inflammation. Immunohistochemistry was used to study the activation of immune cells (microglia) in the retina.

CBD-DMH, CBD alone and CBD+βc were able to decrease the number of activated immune cells (FIG. 7C). While not wishing to be limited by theory, this could provide evidence of a potential mechanism to how CBD-DMH, CBD, and CBD+βc decrease inflammation.

Figure 8:
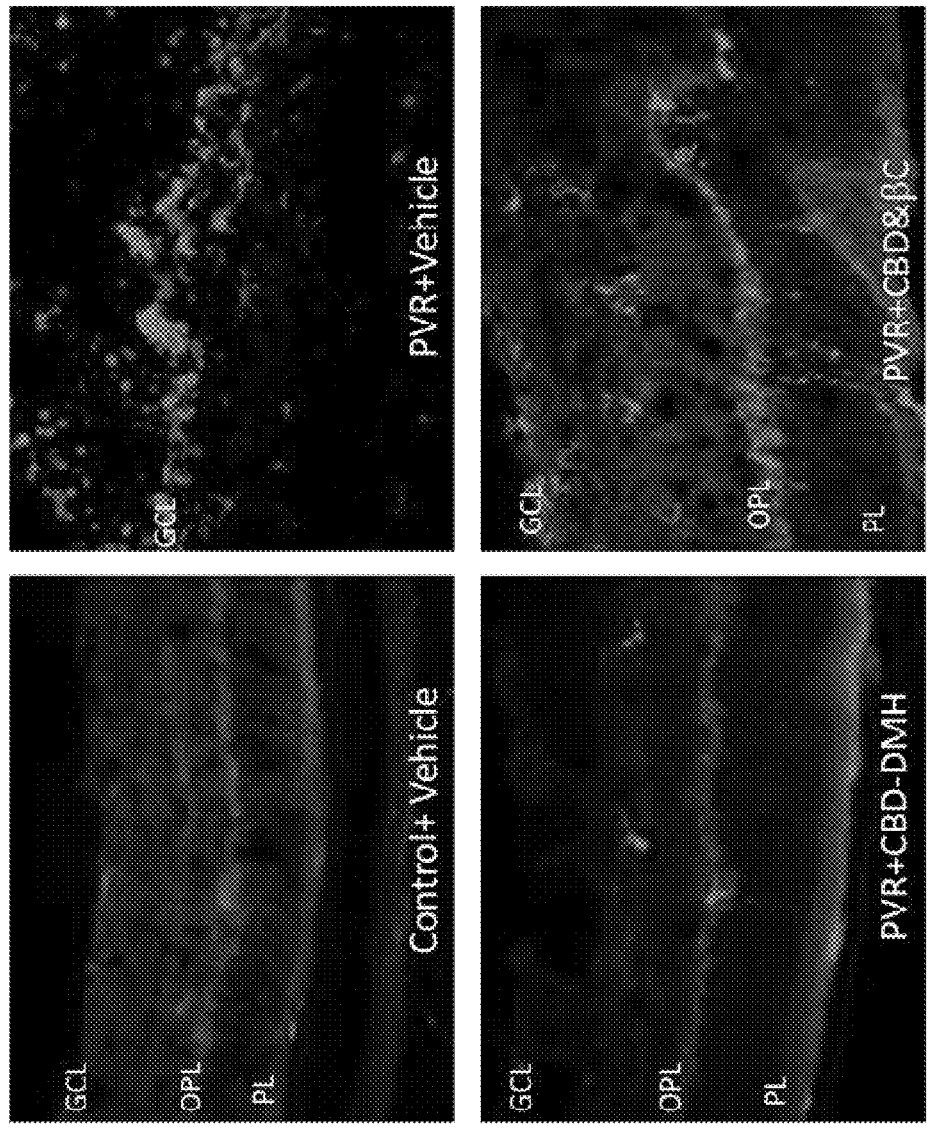
FIG. 8 shows representative images of Iba1 immunohistochemical staining of activated microglia from retinal sections from C57Blk6 mice, either sham control or injected with dispase (0.2 U; 2 μl) to induce PVR and treated with daily ip injections (7 days) of either vehicle (sham control and PVR) or cannabinoid ligands (PVR): top left image: Control+Vehicle; top right image: PVR+Vehicle; lower left image: PVR+CBD-DMH; and lower right image: PVR+CBD+βC.

An increase in IBa1+ microglia (MG) is associated with neuroinflammation. Iba1 is specific to activated MG (Daisuke et al., 2001). Using the selective immunohistochemical label, IBa1 for activated retinal immune cells, microglia, it can be seen that control animals treated with no retinal pathology treated with drug vehicle, there is very sparse labelling for IBa1 positive (IBa1+) cells (FIG. 8, top left). In contrast, in animals with experimental PVR, retinas treated with vehicle have extensive IBa1+ staining for activated microglia (FIG. 8, top right). Iba1+ labeling is substantially reduced in animals with experimental PVR and treated with CBD-DMH (FIG. 8, bottom left) and also (but to a lesser extent) with CBD+beta-C (FIG. 8, bottom right). These results indicate that the synthetic cannabidiol derivative CBD-DMH and CBD+beta-C are able to reduce activated immune cells that contribute to the inflammatory response and pathology in PVR.

Example 4

Effects of Administration of CBD-DMH on Corneal Hyperalgesia

I. Background

The chemical cauterization model of corneal inflammation and hyperalgesia is an established model to look at corneal sensitization and pain. Chemical cauterization of the murine cornea using topical silver nitrate produces nonspecific inflammation followed by chronic behavioral sensitization to subsequent chemical stimuli (modified from Wenk & Honda, 2003).

The corneal reflex blink test provides a behavioral assessment of corneal sensitization and hyperalgesia (decreased pain threshold). The hyperalgesia (defined as increased responsiveness to painful stimuli) is gauged by quantifying the number and frequency of a protective blinking response in the treated eye (stimulus-induced blinking) relative to control non-sensitized eyes (Wenk and Honda 2003). Anti-inflammatory agents and agents that act at targets on nociceptive nerves can reduce development of corneal sensitization and hyperalgesic activity (reduced protective blinking response in response to noxious irritant).

II. Results and Discussion

Figure 9:
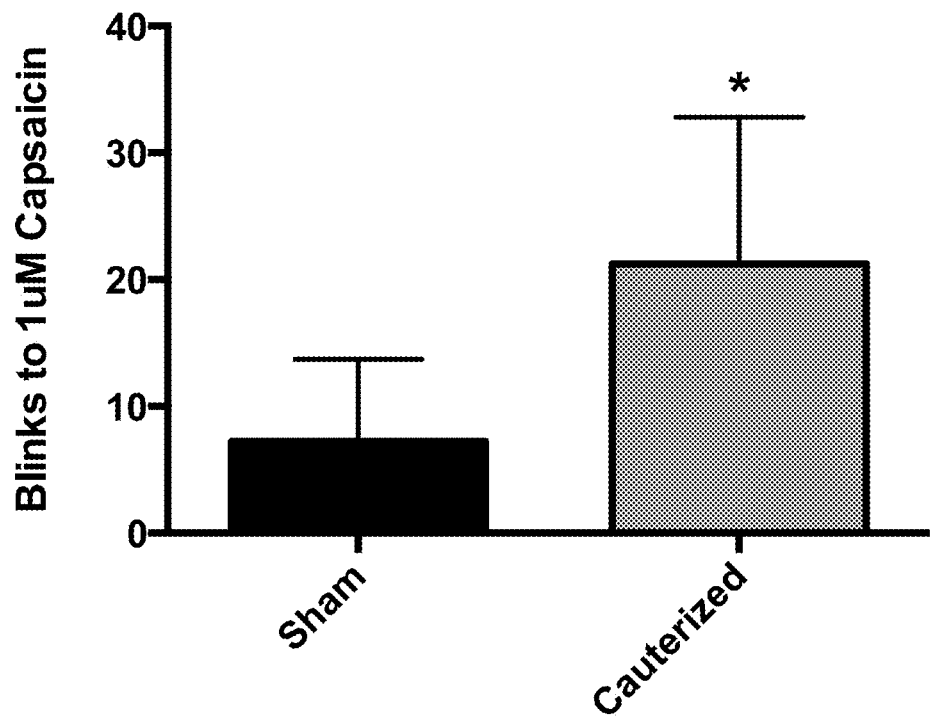
FIG. 9 is a plot comparing number of blinks to an ocular topical application of 1 μM capsaicin following unilateral corneal insult (chemical cauterization) vs. sham (no injury). Increased blinking in cauterized eye (n=6) at 6 hours after injury compared to sham (n=6) indicates higher level of pain. Data are shown as mean±SD*$P<0.05$.
Figure 10:
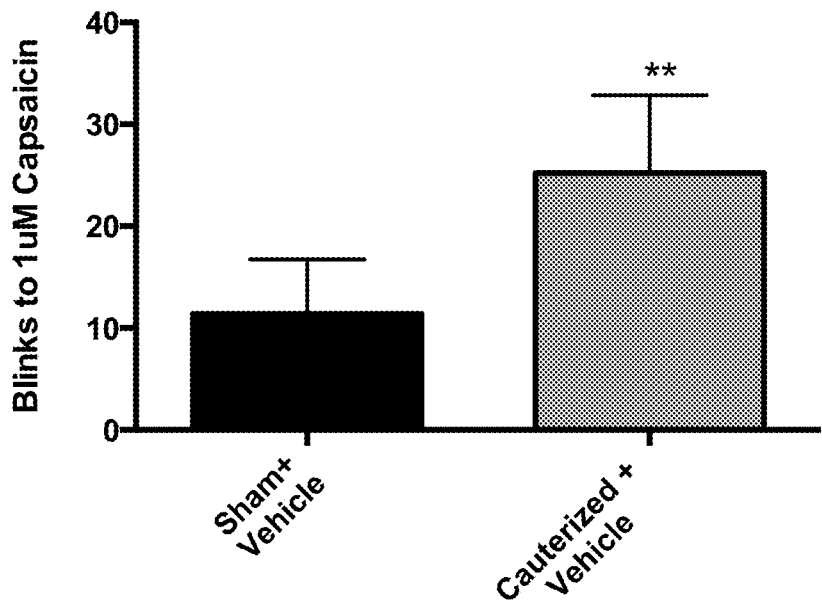
FIG. 10 shows plots showing that unilateral corneal insult (chemical cauterization) in eyes treated with vehicle (no drug) causes corneal hypersensitivity to capsaicin compared to control uninjured vehicle treated eyes (sham) treated eyes: (A) Number of blinks recorded over 1 minute after single ocular topical application of 1 μM capsaicin. Cauterized eyes showed a statistically significant increase in blinks at 6 hour post-injury when compared to the sham (n=6, $p<0.05$); and (B) Data from FIG. 10A plotted as individual points to demonstrate corneal hypersensitization. Data are shown as mean±SD**$P<0.01$; n=6 animals.
Figure 10:
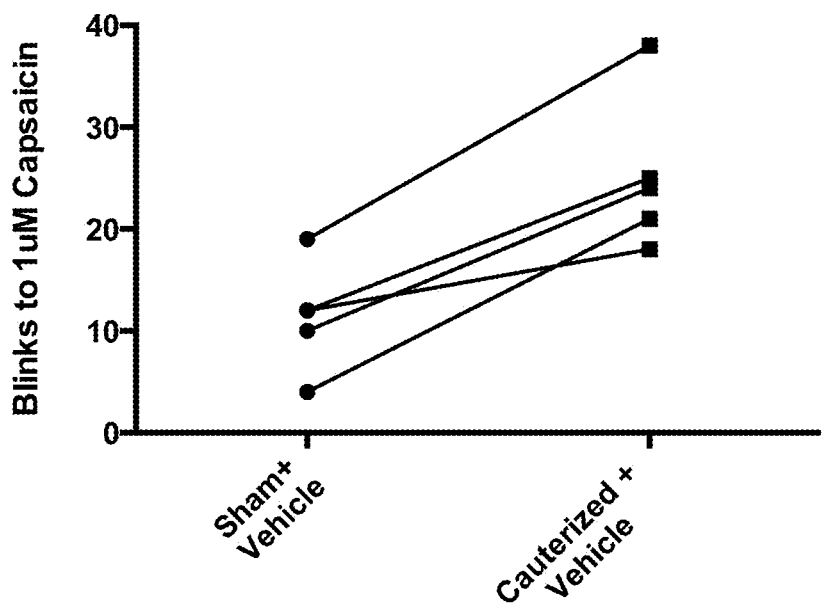
Figure 11:
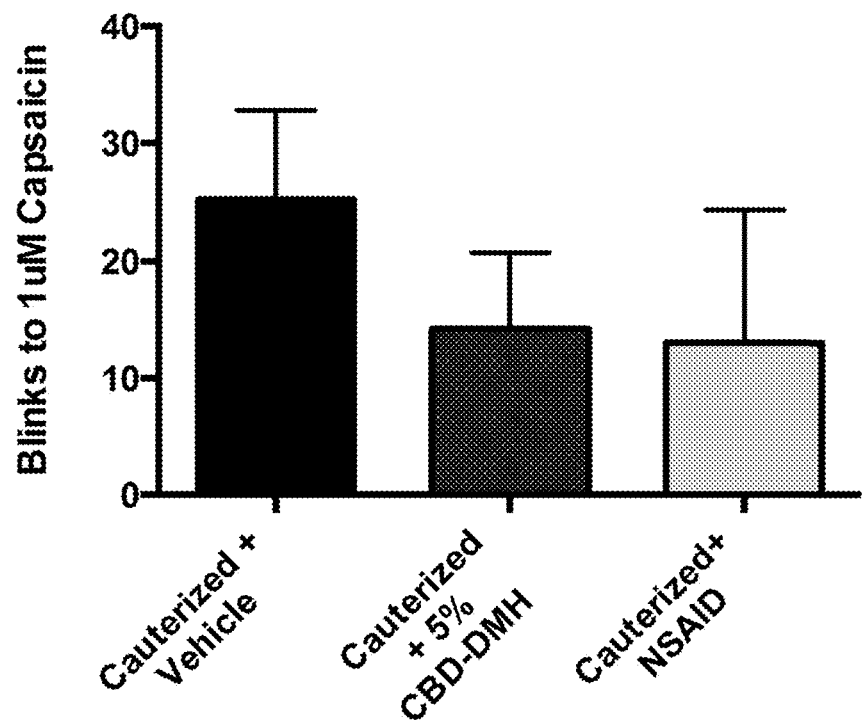
FIG. 11 is a plot of results showing that ocular topical treatment with 5% CBD-DMH reduces hypersensitivity in a comparable matter to ocular topical NSAID. Mean number of blinks recorded over 1 minute after a single ocular topical application of 1 μM capsaicin. Unilateral cauterized eyes were treated with either 3 doses of vehicle (no drug; n=8), 5% CBD-DMH (n=8) or topical NSAID (0.1% Napafenac ophthalmic suspension; n=3). Data are shown as mean±SD.

Using a model characterized by Wenk & Honda, 2003, chemical cauterization using silver nitrate application to the cornea was used to create a corneal hypersensitivity model. Hypersensitivity was determined by assessing blinks to an ocular topical application of 1 µM capsaicin. The blink response is one measure of the level of corneal hyperalgesia. Increased blinking in response to capsaicin in a cauterized eye indicates a higher level of pain (FIG. 9). There was a significant increase in blinks to 1 µM capsaicin in the chemical cauterized eye when compared to the sham control eye (FIG. 10). Ocular topical application of the NSAID Nevanac™ (Nepafenac ophthalmic suspension) eliminated this hypersensitivity (FIG. 11).

Figure 12:
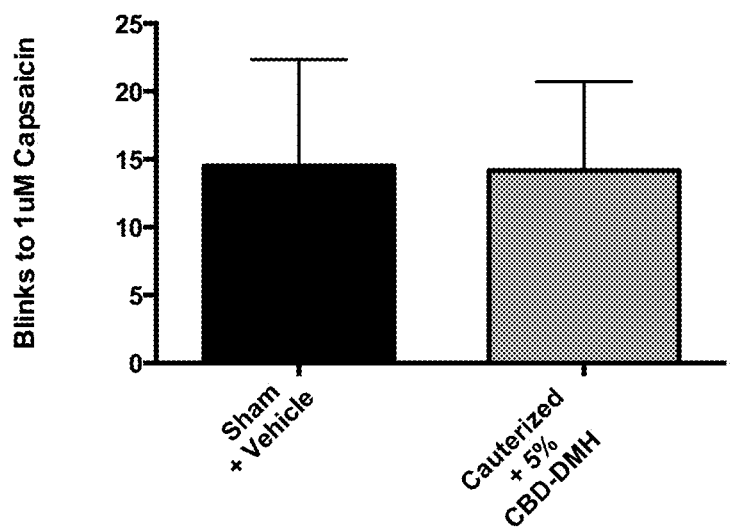
FIG. 12 is a plot of results showing that ocular topical treatment with 5% CBD-DMH eliminates corneal hypersensitivity produced by unilateral corneal insult (chemical cauterization) compared to sham injury. Mean number of blinks recorded over 1 minute after single ocular topical application of 1 μM capsaicin. Sham eyes received vehicle (no drug) and cauterized eyes were treated with 3 doses of 5% CBD-DMH. Treatment with CBD-DMH eliminated hypersensitivity to capsaicin (n=8, $P>0.05$).

Evaluation of CBD-DMH showed that it further eliminates this hypersensitivity, showing a statistically significant decrease in blinks to 1 µM capsaicin when in the chemical cauterized eye when compared to the sham control eye (FIG. 12). Beta-C has also been tested in this model and appeared to also produce a reduction in hyperalgesia.

Summary of Examples 1-4

Table 3 provides a summary of models, treatments and doses used in the above-described studies of the disclosure.

TABLE 3

Figure 2:
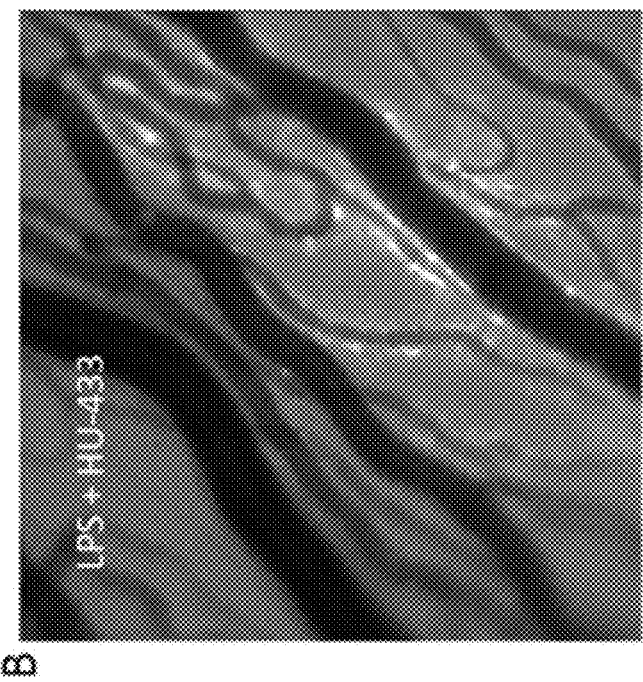
FIG. 2 shows representative intravital microscopy images in rat eye showing adherent leukocytes at 6 hours after intravitreal injection of (A) LPS; and (B) LPS+HU-433 (0.1 mg·kg$^{-1}$) showing that administration of the cannabinoid, HU-433, ameliorates the effects of LPS as demonstrated by fewer adherent leukocytes. White arrows in FIG. 1A indicate adherent leukocytes.
Figure 2:
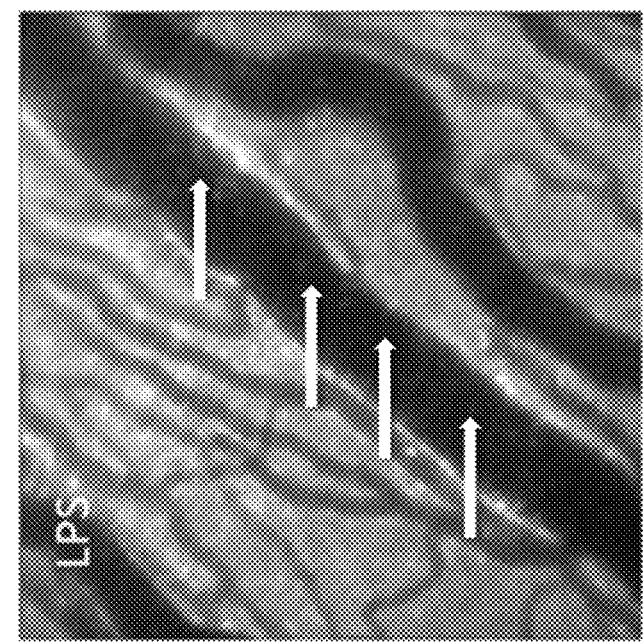
Figure 7:
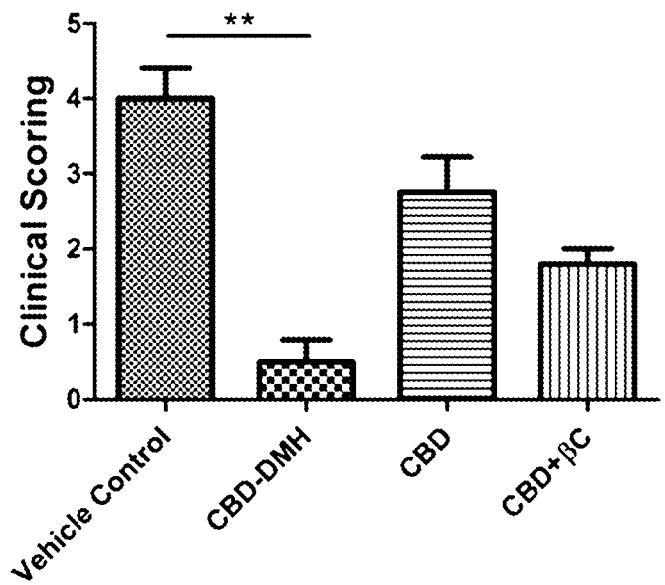
FIG. 7 shows results of proliferative retinopathy (PVR) evaluation in C57Blk6 mice injected with dispase (0.2 U; 2 μl) and treated with daily ip injections (7 days) of vehicle (no drug) or cannabinoid ligands: Vehicle, CBD-DMH (10 mg/kg), CBD (10 mg/kg), and CBD (10 mg/kg)+β-Caryophyllene (βC; 20 mg/kg). (A) Clinical evaluation of PVR. The severity of the PVR was determined on a scale of 0-5, with 0 (no disease) to 5 (completely degenerated eye). (B) Histopathologic score in PVR (or control) mice was assessed using H&E staining and was evaluated with the scoring system of 0 (no disease) to 4 (severely damaged ocular tissue). The evaluation was based on the degree of retinal damage, the infiltration of inflammatory cells, presence/absence of exudates and formation of granulomas. (C) Average microglia (MG) count per retinal section/animal. Data are shown as mean±SEM*$P<0.05$.
Figure 7:
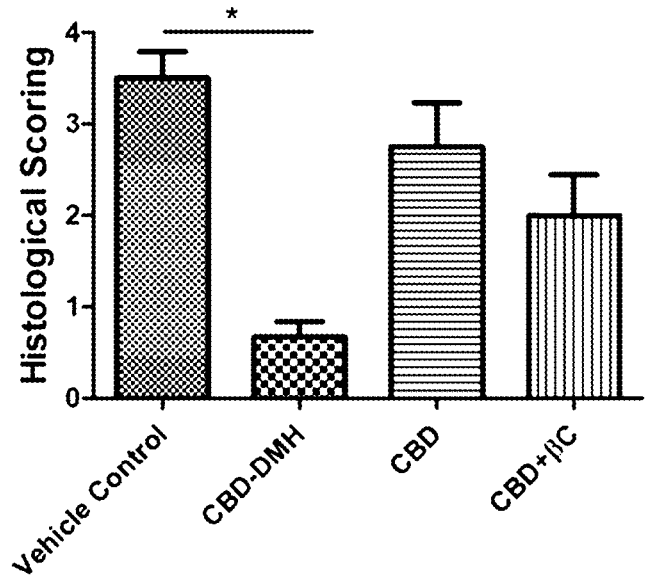
Figure 7:
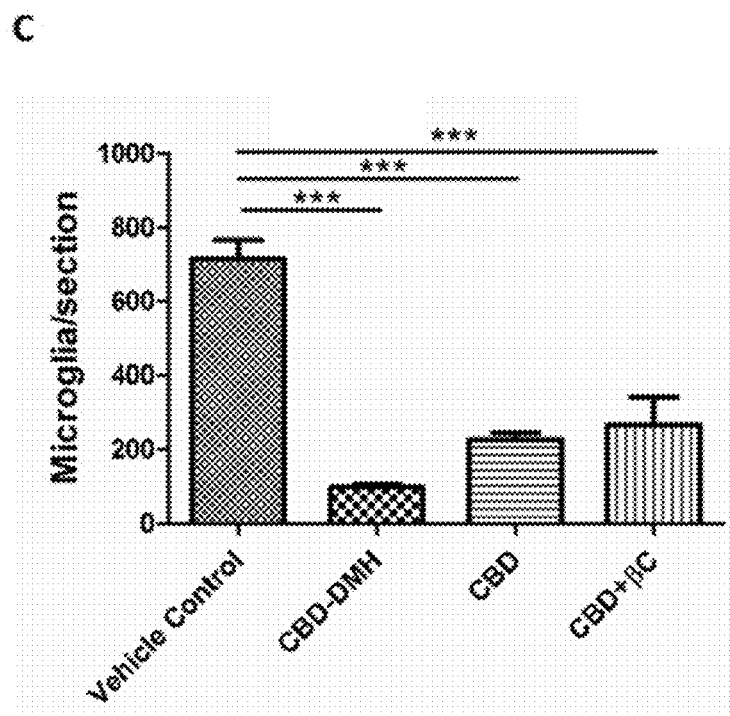

| Figure | Model | Treatment | Dose |
| --- | --- | --- | --- |
| FIG. 1 | Endotoxin-induced Uveitis | LPS + HU-433 | 1, 0.1, 0.01, 0.001 mg/kg |
| FIG. 2 | Endotoxin-induced Uveitis | LPS + HU-433 | 0.1 mg/kg |
| FIG. 3 | Endotoxin-induced Uveitis | LPS + HU-433 | 1, 0.1, 0.01, 0.001 mg/kg |
| FIG. 4 | Endotoxin-induced Uveitis | LPS + HU-433 | 1, 0.1, 0.01, 0.001 mg/kg |
| FIG. 5 | Experimental Uveitis | LPS + CBD-DMH | |
| FIG. 6 | Experimental Uveitis | LPS + CBD-DMH | |
| FIG. 7 | PVR | CBD-DMH | 10 mg/kg |
| | | CBD | 10 mg/kg |
| | | CBD + βC | 10 mg/kg + 20 mg/kg |
| FIG. 8 | PVR | CBD-DMH | 10 mg/kg |
| | | CBD + βC | 10 mg/kg + 20 mg/kg |
| FIG. 9 | Corneal Hyperalgesia | — | — |
| FIG. 10 | Chemical cauterization causes corneal hypersensitivity to capsaicin. | | |
| FIG. 11 | Corneal Hyperalgesia | CBD-DMH | 5% solution |
| FIG. 12 | Corneal Hyperalgesia | CBD-DMH | 5% solution |

Example 5

Other Animal Models of Intraocular Inflammation

Receptor knock-out models: Genetic receptor null models (murine) are available for the following receptor targets: $CB_2$; Receptor knock-outs (−/−) are used as controls for further validation of drug targets in models of ocular inflammation and neuropathic pain.

Example 6

In Vitro Analysis of CBD and CBD-DMH

I. Materials and Methods

Methods are modified from LaPrairie et al., 2014 a, b.

Cell Culture

HEK cells were maintained at 37° C., 5% $CO_2$ in Dulbecco's Modified Eagle's Medium (DMEM) supplemented with 10% Fetal Bovine Serum (FBS) and $10^4$ U·mL$^{-1}$ Pen/Strep.

Drugs

Drug stocks were made up in DMSO [CBD, CBD-DMH and CP 55,940] and diluted to final solvent concentrations of 0.1%. CBD and CP 55,940 were purchased from Tocris Bioscience (Bristol, UK).

CP 55,940 is a full (orthosteric) agonist of CB1 and CB2, which is commonly used in studies of the activity of compounds at these receptors. This agonist binds to CB1 and CB2 to maximally activate the receptor and G protein coupled signaling pathways with resultant alterations in downstream signaling molecules and functional changes.

On- and In-Cell™ Western

For In-Cell™ western analyses, cells were fixed for 10 min at room temperature with 4% paraformaldehyde and washed three times with 0.1 M PBS for 5 min each. Cells were incubated with blocking solution (0.1 M PBS, 5% normal goat serum, 0.3% TritonX-100, in $dH_2O$) for 1 h at room temperature. Cells were treated with primary antibody diluted in antibody dilution buffer [0.1 M PBS, 1% (w/v) BSA, 0.3% TritonX-100, in $dH_2O$] overnight at 4° C. Primary antibody solutions were: pERK1/2(Tyr205/185) (1:200), ERK1/2 (1:200), pPLCβ3(S537) (1:500), PLCβ3 (1:1000), or β-actin (1:2000; Santa Cruz Biotechnology). Cells were washed three times with 0.1 M PBS for 5 min each. Cells were then incubated in IR$^{CW800dye}$ (1:500; Rockland Immunochemicals, Gilbertsville, Pa., USA) for 1 h at room temperature. Cells were washed three times with 0.1 M PBS for 5 min each. Cells were allowed to air-dry overnight.

In-Cell™ data were collected using the Odyssey Imaging system and software (version 3.0; Li-Cor, Lincoln, Nebr., USA).

Statistical Analyses

Goodness of fit to non-linear regression models was tested in GraphPad (v. 5.0, Prism). Concentration-response curves (CRC) are shown in each figure according to the model with the best fit. Pharmacological statistics were obtained from non-linear regression models. Statistical analyses were two-way analysis of variance (ANOVA), as indicated, using GraphPad. Homogeneity of variance was confirmed using Bartlett's test. The level of significance was set to $P<0.001$ or $<0.01$, as indicated. Results are reported as the mean±the standard error of the mean (SEM) or mean and 95% confidence interval, as indicated, from at least 4 independent experiments.

II. Results and Discussion

Figure 13:
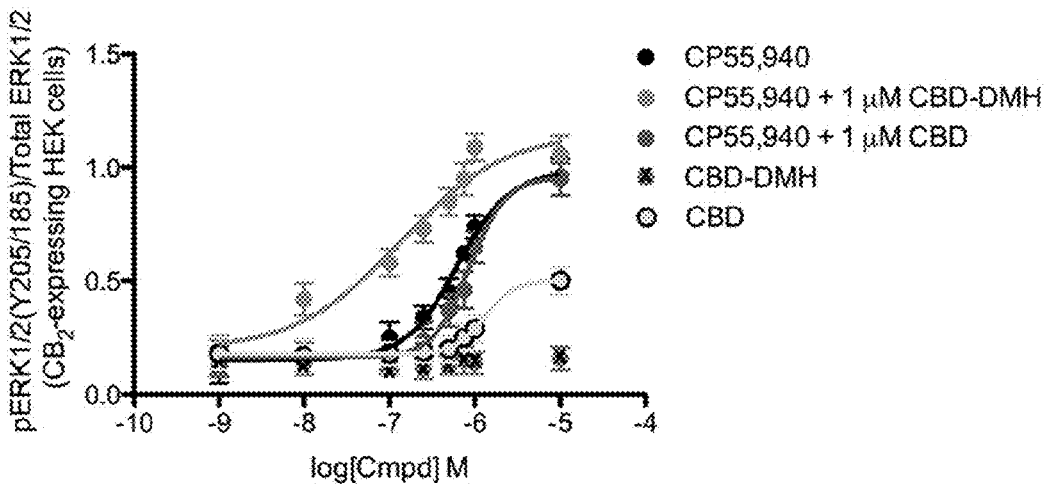
FIG. 13 shows plots showing the results of in vitro studies of CBD and CBD-DMH: A: HEK 293A cells transiently transfected with hCB2 were treated with 0.001-10 μM of the indicated compound±1 μM CBD-DMH or CBD for 10 min. Following 10 min treatment, cells were fixed with 4% paraformaldehyde and used in In-Cell™ western assays for the detection of phosphorylated and total extracellular signal regulated kinase (ERK) according to the methods described in Laprairie et al. (2014 J Biol Chem); B: HEK 293A cells transiently transfected with hCB2 were treated with 0.001-10 μM of the indicated compound±1 μM CBD-DMH or CBD for 10 min. Following 10 min treatment, cells were fixed with 4% paraformaldehyde and used in In-Cell™ western assays for the detection of phosphorylated and total PLCβ3 according to the methods described in Laprairie et al. (2014 J Biol Chem); C: HEK-CRE reporter cells stably expressing firefly luciferase under the regulatory control of a promoter containing tandem cAMP-response elements and transiently transfected with hCB2 were treated with 10 μM forskolin for 30 min followed by 0.001-10 μM of the indicated compound±1 μM CBD-DMH or CBD for an additional 30 min. Following 30 min treatment cells were lysed and cAMP activity was measured at 405 nm (RLU, relative light units). Concentration-response curves were fit using non-linear regression analysis (GraphPad Prism, version 5.0). Data are displayed as the mean±S.E.M from 4 independent experiments.
Figure 13:
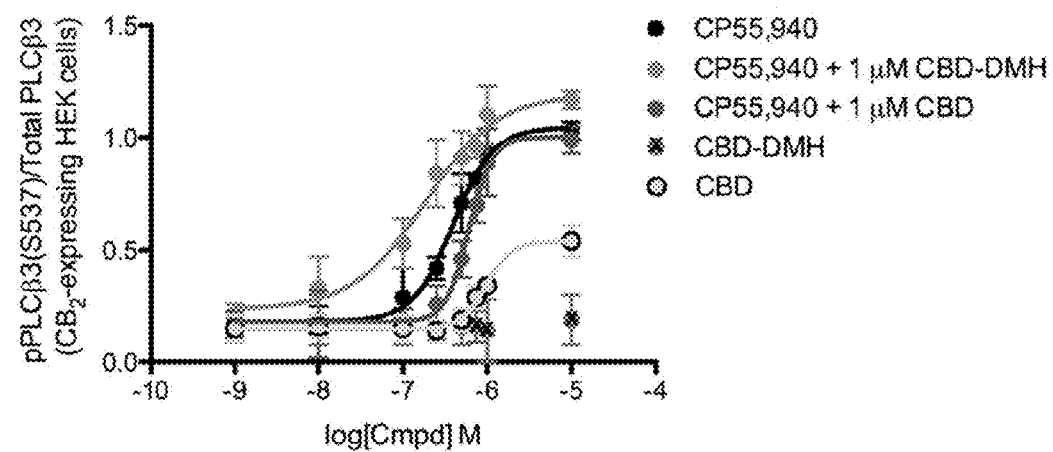
Figure 13:
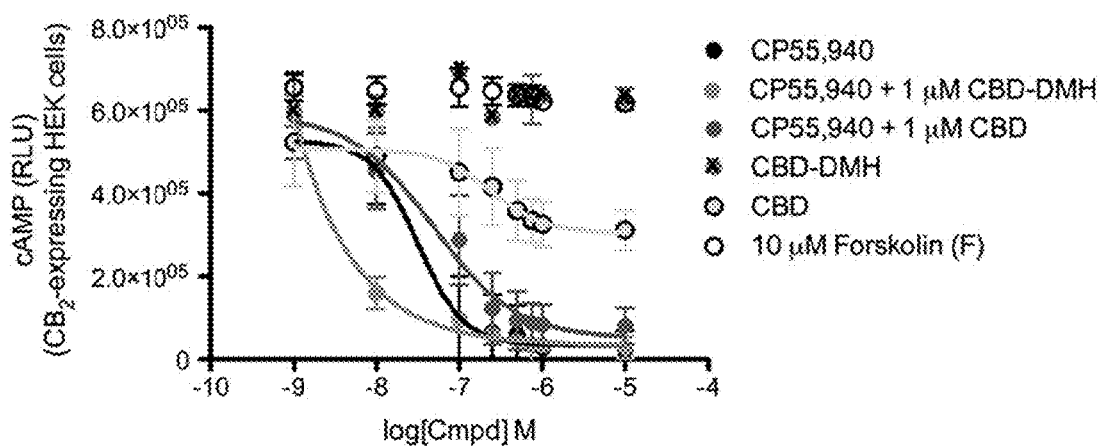

The results of this study are shown in FIGS. 13A-C and Tables 4-6. The results indicate that CBD-DMH is a positive allosteric modulator (Christopoulos and Kenakin, 2002) of $CB_2$-dependent G protein signalling and enhances the potency and efficacy of the orthosteric CB2 agonist, CP55940, to activate CB2 coupled G protein signalling pathways (summarized in Tables 4-6). CBD-DMH does not activate CB2 in the absence of the orthosteric agonist, CP55940. In these assays, CBD is a partial agonist of $CB_2$-dependent G protein signalling (summarized in Tables 4-6).

The following tables show the mean $EC_{50}$ and $E_{Max}/E_{Min}$ values for the effects of CBD-DMH and CBD on CP55,940-dependent $G\alpha_{i/o}$ ERK phosphorylation, cAMP and $G\alpha_q$ PLCβ3 phosphorylation.

TABLE 4

ERK ($G\alpha_{i/o}$)

|  |  | $EC_{50}$ (nM) ± SEM | $E_{max}$ (%) ± SEM* |
|---|---|---|---|
| $CB_2$ | CP55,940 + 1 µM CBD-DMH | 135.70 ± 22.58 | 117.17 ± 12.01 |
|  | CP55,940 + 1 µM CBD | 865.40 ± 6.62 | 97.36 ± 7.09 |
|  | CBD-DMH | — | — |
|  | CBD | 1286.00 ± 22.98 | — |
|  | CBD-DMH + 500 nM CP55,940 | 39.90 ± 64.98 | 113.11 ± 22.96 |
|  | CBD + 500 nM CP55,940 | 348.70 ± 78.69 | 46.83 ± 12.33 |

*Calculated as a percentage of the maximal response to the agonist CP 55,940

TABLE 5

PLCβ3 ($G\alpha_q$)

|  |  | $EC_{50}$ (nM) ± SEM | $E_{max}$ (%) ± SEM* |
|---|---|---|---|
| $CB_2$ | CP55,940 + 1 µM CBD-DMH | 185.30 ± 18.43 | 114.37 ± 17.06 |
|  | CP55,940 + 1 µM CBD | 609.50 ± 5.93 | 95.98 ± 12.36 |
|  | CBD-DMH | — | — |
|  | CBD | 977.90 ± 7.80 | 51.68 ± 7.04 |
|  | CBD-DMH + 500 nM CP55,940 | 196.70 ± 9.24 | 102.01 ± 6.32 |
|  | CBD + 500 nM CP55,940 | 699.30 ± 11.80 | 43.59 ± 3.98 |

*Calculated as a percentage of the maximal response to the agonist CP 55,940

TABLE 6 cAMP

|  |  | $EC_{50}$ (nM) ± SEM | $E_{min}$ (%) ± SEM† |
|---|---|---|---|
| $CB_2$ | CP55,940 + 1 µM CBD-DMH | 48.27 ± 37.49 | 153.24 ± 23.13 |
|  | CP55,940 + 1 µM CBD | 31.39 ± 31.37 | 103.01 ± 12.64 |
|  | CBD-DMH | — | — |
|  | CBD | 237.30 ± 47.55 | 928.15 ± 24.61 |
|  | CBD-DMH + 500 nM CP55,940 | 241.85 ± 48.33 | 475.19 ± 11.91 |
|  | CBD + 500 nM CP55,940 | 353.96 ± 49.37 | 423.98 ± 88.16 |

†Calculated as a percentage of the maximal inhibition of cAMP in response to the agonist CP 55,940

Example 7

Topical Treatment with CBD-DMH or Liposomal 0.1% THC

In a model of corneal hyperalgesia, chemical cauterization of the cornea produces corneal epithelial damage, corneal edema and inflammation. This results in an increased response to a previously mild noxious stimuli observed by 6-8 hours after the injury. The effect of repeated dosing with the CB2 allosteric modulator, CBD-DMH, or the cannabinoid $\Delta^9$THC that acts as an agonist at CB1 and CB2 receptors, was tested to determine if these agents could prevent the development of hyperalgesia. Animals were videoed before and after capsaicin administration using a handheld device and video images were analyzed off-line by an observer blinded to the treatment. A pain score was generated as the number of protective blinks or eye wipes in response to capsaicin within 1 minute of capsaicin application.

Figure 14:
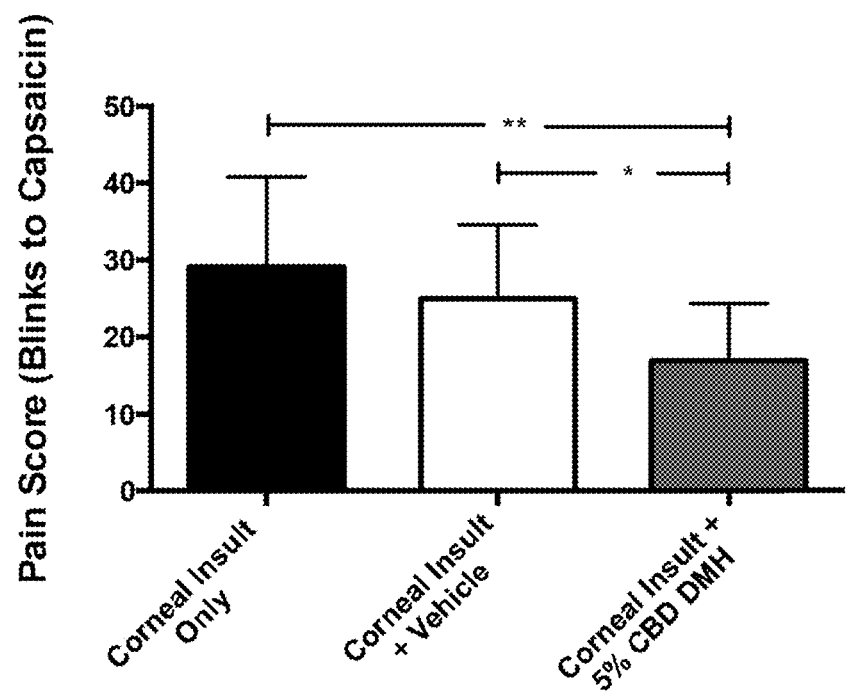
FIG. 14 shows plots showing that topical treatment with 5% CBD-DMH or liposomal 0.1% THC reduces hypersensitivity caused by bilateral and unilateral corneal chemical insult (chemical cauterization). A: Mean number of blinks recorded for 1 minute at 6 hours post corneal insult by silver nitrate after a single topical application of 1 μM capsaicin. Corneal insult was left untreated (Corneal insult only; n=14), or received 3 doses of vehicle (Corneal insult+ vehicle; n=17), or 5% CBD-DMH (Corneal insult+5% CBD-DMH; n=14). B: Mean number of blinks recorded for 1 minute captured 6 hours post corneal insult by silver nitrate after single topical application of 1 μM capsaicin.
Figure 14:
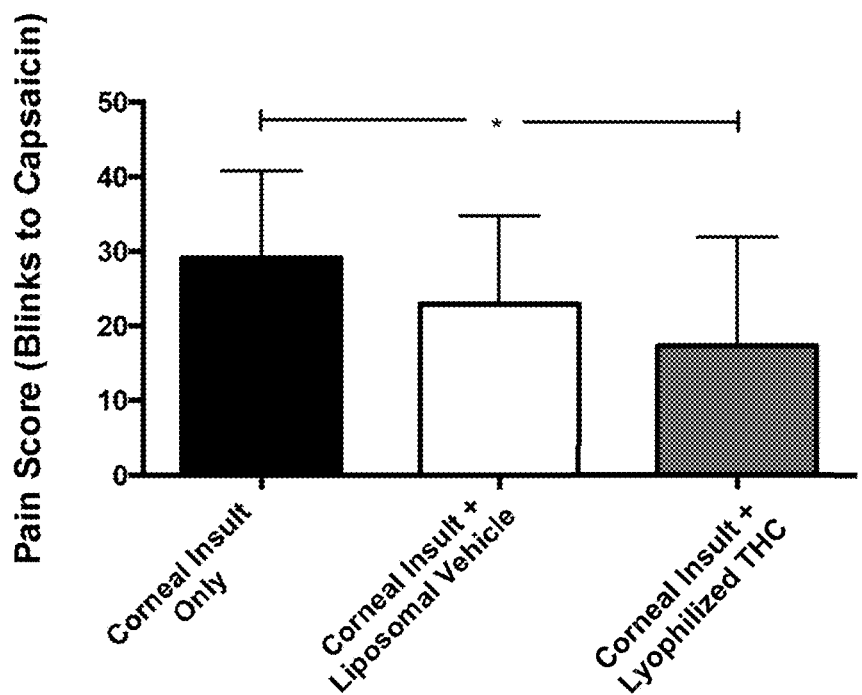

Topical treatment with 5% CBD-DMH or liposomal 0.1% THC was found to reduce hypersensitivity caused by corneal chemical insult (FIG. 14).

FIG. 14A shows the mean number of blinks recorded for 1 minute at 6 hours post corneal chemical insult by silver nitrate after a single topical application of 1 µM capsaicin. Corneal insult was left untreated (n=14), or received 3 doses of vehicle (n=17), or 5% CBD-DMH (n=14). Eyes treated with 5% CBD-DMH showed a statistically significant decrease in blinks compared to untreated and vehicle treated eyes. (1-way ANOVA $F_{2,42}$=5.811, p<0.05).

FIG. 14B shows the mean number of blinks recorded for 1 minute captured 6 hours post corneal insult by silver nitrate after single topical application of 1 µM capsaicin. Corneal insult was left untreated (n=14), or treated with 3 doses of empty liposomes (n=14), or liposomal THC (n=16). Eyes treated with THC showed a statistically significant decrease in blinks compared to untreated but not to vehicle-treated eyes. (1-way ANOVA $F_{2,41}$=3.155, p=0.053).

Example 8

Histological Examination of Corneal Edge Region

Corneal chemical injury results in inflammation, with recruitment of immune cells (e.g neurotrophils) to the injury site and edema. This can be visualized histologically in paraformaldehyde tissue sections (6-12 µm) using for example, hematoxylin-eosin stain or with fluorescent immunohistochemistry using antibodies that label specific immune cell populations such as neutrophils.

Histological examination (e.g. hematoxylin-eosin stain) of the corneal edge region after silver nitrate chemical insult was undertaken (FIG. 15). FIG. 15A shows an exemplary image of the corneal edge region of the untreated left eye removed post-mortem 12 hours after corneal insult by silver nitrate. The untreated left eye (FIG. 15A) shows increased immune cell infiltration and corneal edema compared to the right eye cornea treated with 3 doses of topical liposomal 0.1% THC and 2% CBD-DMH (FIG. 15B). Topical cannabinoids were administered at 30, 60 and 120 minutes after corneal insult by silver nitrate application.

FIG. 15C shows an exemplary image of the corneal edge of the untreated left eye stained with LY-6 antibody showing increased staining of neutrophils post-mortem 12 hours after corneal insult following silver nitrate application. The untreated left cornea (FIG. 15C) has increased immune cell infiltration and corneal edema compared to the right eye cornea (FIG. 15D) treated with 3 doses of topical liposomal 0.1% THC and 2% CBD-DMH administered at 30, 60 and 120 minutes after corneal insult by silver nitrate.

Combinations of cannabinoids, including the non-psychotropic cannabinoid, CBD-DMH, and the phytocannabinoid, THC, reduced inflammation (decreased edema and reduced neutrophils accumulating at the injury site) after chemical cauterization. Combination treatments provided improved therapeutic index, with significant anti-inflammatory actions seen at lower doses, compared to either agent used individually.

Example 9

Administration of CBD-DMH or a Combination of CBD-DMH and a Selective CB$_2$ Receptor Agonist Using a PVR Model I. Introduction Proliferative vitreoretinopathy (PVR) is the most common, sight-threatening complication of retinal detachment, severe ocular trauma, or inflammation. PVR is characterized by the proliferation and migration of retina pigmented epithelial (RPE) cells and fibroblasts, to form contractile membranes on and beneath the retina, and immune cells activation and their infiltration of ocular tissues. The standard treatment of PVR is a vitreous surgery, which itself can lead to severe complications, including loss of vision. There are no currently available effective pharmacological treatments, therefore development of new therapeutics is useful for the treatment of PVR.

The endocannabinoid system, composed of lipid-derived endogenous ligands, enzymes responsible for their synthesis and degradation, and cannabinoid receptor type 1 (CB1) and type 2 (CB2), is an emerging target for a number of inflammatory conditions. It has been shown that the modulation of CB2 receptor, found within the peripheral tissues has a significant effect on the inflammatory response. Animals deficient for CB2R develop more severe PVR, as compared to their wild type controls. Elevated microglia counts, retina folds and retinal detachment were evident in animals lacking CB2R. This suggests that targeting CB2R may provide a useful target for treatment of PVR.

II. Objective

The objective of the study is to evaluate the anti-inflammatory and anti-fibrotic actions of non-psychotropic cannabinoids, including CBD-DMH alone, or in combination with selective CB2R agonists, including HU308, HU433 and CBD.

III. Methods

PVR is induced in C57Blk mice with an intravitreal injection of dispase (0.2 U µl$^{-1}$; Sigma), a neutral protease which cleaves basement membrane into the dorso-lateral quadrant of the left eye. This results in a chronic inflammatory response, as well as the formation of retinal folds and retinal detachment. Saline is injected into the dorso-lateral quadrant of the left eye in control mice. At 1 week post injection the external morphology of the eye is evaluated by clinical scoring, on the scale 0-5, with 0 (no disease) to 5 (completely degenerated eye). Then, the animals are sacrificed and eyes enucleated and prepared for histological or immunohistochemical staining. The internal tissue histology of the eye is visualized by haematoxylin and eosin (H&E) staining, and scored on the scale 0-4, with 0 (no disease) to 4 (severely damaged ocular tissue) under a light microscope. The immunohistochemical staining for microglia (anti-rabbit Iba1) and astrocytes (anti-rabbit GFAP) is used to evaluate the degree of the inflammatory response.

IV. Cannabinoid Treatments

The animals are treated with daily topical applications of CBD-DMH (0.5-5%) alone or in combination with CB2R agonists HU308 (0.1-1%), HU433 (0.1-1%), and CBD (1-2%). The data is analyzed by One-Way ANOVA analysis, followed by Kruskal-Wallis test. $p<0.05$ is considered significant.

V. Results

The inventors expect that the topical daily treatment with CBD-DMH alone or in combination with CB2R agonists HU308, HU433 and CBD will decrease the degree of inflammatory response seen in PVR, as indicated by the reduced number of activated microglia, and astrocytes, and a reduction in fibrosis. In addition, the inventors expect to see improvement in overall morphology of the eye, and in the histological outcomes. The combination of CBD-DMH and other cannabinoids that act at CB2, are expected, for example, to allow for increased actions of these cannabinoids with therapeutic efficacy achieved at lower doses of each of the respective cannabinoids.

Example 10

Administration of CBD-DMH or a Combination of CBD-DMH and a Selective CB$_2$ Receptor Agonist Using a Uveitis Model I. Purpose To determine the anti-inflammatory efficacy of synthetic CB2R agonists (CBD-DMH, HU 308, HU 433, CBD and µ-caryophyllene) to inhibit leukocyte-endothelial interactions and tissue pathology in a mouse experimental model of acute endotoxin-induced uveitis (EIU) using intravitreal injection of lipopolysaccharide (LPS) in WT and CB2 null mice.

II. Materials and Methods

Grouping and Time Course:

Two Different EIU Experimental Groups are Examined in Mice:

Group A: Intravital microscopy (IVM) to visualize leukocyte-endothelium interactions at 6 hours after induction of EIU and topical application of CB$_2$ agonist to LPS injected eye (single dose, immediately following LPS intraocular injection) in BALB/c mice.

Group B: IVM at 6 hours after induction of EIU and topical application of CB$_2$ agonist to LPS injected eye (single dose, immediately following LPS intraocular injection) in CB2R$^{-/-}$ mice.

Tested Compounds:

CBD-DMH, HU 308, HU 433, CBD, β-caryophyllene or combinations thereof are tested.

Drug Treatments:

Animals are lightly sedated under low dose pentobarbital, 5 µl of drug solution or soyabean oil emulsion vehicle is applied as an ophthalmic drop to LPS injected eye, Tear-Gel® is applied to the contralateral eye to prevent corneal desiccation.

CBD-DMH (0.5 or 5%) together with (HU308 or HU433 at 0.1 or 1%), CBD (1-2%) or β-caryophyllene (1-2%) is used.

Intravitreal Injection of LPS to Induce Uveitis:

Mice are anesthetised prior to induction of uveitis with 5% isoflurane in 100% oxygen and depth of anesthesia is monitored via toe pinch test. The head of the animal is immobilized, and the sclera of the left eye is punctured with a 30-gauge needle at the dorsonasal quadrant at approximately the level of the equator. LPS (125 ng/µl; Sigma-Aldrich, Oakville, ON, Canada) is diluted in sterile 0.9% sodium chloride saline solution. Intravitreal injections are made under microscopic control with a Hamilton syringe (Hamilton Company, Reno, Nev., USA), fitted with a 30 G1/6 needle. Mice receive 2 µl of the LPS solution. To avoid touching the lens or causing any damage to the eye, the tip of the needle is directed towards the posterior pole and only the bevelled tip (2-3 mm) is allowed to enter the vitreal cavity. The needle is held in place for another 5 seconds to avoid leakage of the LPS via the sclerostomy (injection site). Following the injection, the sclerostomy site is closed using tissue adhesive to prevent any leakage. After the procedure, the eye of each animal is checked for bleeding or swelling. Only animals with no bleeding or swelling are used.

In Vivo Imaging:

The technique of intravital microscopy (IVM) is used for in vivo investigation of leukocyte recruitment. The epifluorescence video microscope is focused on the iridial microcirculation, which allows for imaging of the leukocyte-endothelial interactions. Throughout IVM, the animal's head is made stationary by placement in a rotational head holder and a cover slip is placed over the left eye of the animal. The iris is divided into four equal quadrants by drawing two superficial lines, lengthwise and widthwise. IVM is carried out at each of these quadrants. In each video, leukocyte recruitment is observed and recorded for 30 seconds each. Evaluation of all the videos is carried out off-line.

IVM Analysis:

Several videos of each quadrant are recorded for 30 seconds. Leukocyte adhesion in iridial venules is the parameter analyzed. Adherent leukocytes is defined as the number of leukocytes during the 30 second observations period that did not detach from the cylindrical endothelial surface. The number of adherent leukocytes within each vessel segment is calculated by measuring the diameter and length of vessel segment studied, assuming a cylindrical geometry of blood vessel. Adherent leukocytes are expressed as number of cells per $mm^2$ of endothelial surface.

IVM Data Analysis:

Results are analyzed using the software Prism 5 (GraphPad Software, La Jolla, Calif., USA). All data are expressed as means±deviation (SD). Groups are tested for significance using one-way analysis of variance (ANOVA) with a Dunnett's post hoc test, comparing all experimental groups to the vehicle treated group. Significance is considered at $p<0.05$.

III. Results and Discussion

Testing was done with an acute experimental model of ocular inflammation (pan-uveitis) to examine the disease-preventing role of cannabinoid receptor ligands (Szczesniak et al., 2013, 2012; Toguri et al., 2014). In a sterile EIU model, cannabinoids that act at CB2R, reduce immune cell recruitment (leukocytes in the iris and retinal microvasculature), decreased levels of proinflammatory mediators, improved iridial blood flow and reduced tissue pathology (Toguri et al., 2014). The inventors expect that topical treatment with drug combinations of CB2R positive allosteric modulator, CBD-DMH, and the CB2 agonists, HU308, HU433, CBD or β-C will result in improved therapeutic index for reducing ocular inflammation in the experimental model of EIU; doses of cannabinoids subthreshold for reducing leukocyte recruitment (inflammation) now produce a significant reduction in immune cell recruitment and pro-inflammatory cytokines with improved iridial blood flow and less tissue damage. The inventors also expect that combinations of CBD-DMH with HU 308 or HU 433 will be more useful in mitigating intraocular inflammation than combinations of CBD-DMH with either CBD or β-caryophyllene and that combinations of CBD-DMH+ either CBD or β-caryophyllene will be more useful than either of the latter CB2 agonists alone.

Example 11

Administration of CBD-DMH, or a Combination of CBD-DMH and a Non-Selective Cannabinoid Using a Corneal Hyperalgesia Model I. Introduction Human and animal tissues possess an endogenous system that is composed of two G protein-coupled cannabinoid receptors, cannabinoid type 1 ($CB_1$) and type 2 ($CB_2$) receptors. This system plays a key role in inflammation and pain modulation. In addition to the principal psychotropic cannabinoid, $\Delta^9THC$ (THC), other phytocannabinoids, including CBD and $\Delta^8THC$ also relieve inflammatory disease and neuropathic pain and interactions between constituent phytocannabinoids may lead to additional useful therapeutic effects. Phytocannabinoids and cannabinoids that can activate CB2 may have utility in ocular inflammation and neuropathic pain.

In the eye, work has indicated that activation of CB2 receptors specifically, as well as CB1 receptors, can alleviate ocular inflammation (Toguri et al., 2014; Toguri et al., submitted, 2015). The anti-inflammatory actions of CB2 agonist drugs are consistent with upregulation of CB2 receptors during inflammation. In the cornea, it has been demonstrated that the cannabidiol derivative, CBD-DMH (which acts as a positive allosteric modulator at CB2 and testing will show acts as a weak agonist at CB1), reduces development of corneal hyperalgesia and allodynia after corneal chemical burn and trauma.

II. Objectives

To show: 1) The efficacy of the non-selective cannabinoids, $\Delta^9THC$, $\Delta^8THC$, WIN 55,212-2 and CP 55,940 either alone or in combination with the cannabidiol derivative, CBD-DMH, to reduce development of corneal hyperalgesia and allodynia and improve corneal wound healing after chemical burn and trauma in wild-type and CB2 genetic knock-out animals.

III. Experimental Approach

A model of silver nitrate cauterization to generate corneal inflammation and hyperalgesia is used (modified from Wenk & Honda, 2003). This model uses Balb/c mice and Balb/c $CB2^{-/-}$ mice and examines the development of hyperalgesia by quantifying the number and frequency of a protective blinking response in the treated eye (stimulus-induced blinking) relative to control non-sensitized eyes in response to a noxious stimulus test (Capsaicin 1 μM). At 6 or 8 hours after chemical cauterization, the behavioral or pain response (blinks to topical capsaicin) is determined. Increased blinking in response to capsaicin in the chemical cauterized eye when compared to the sham control eye indicates a higher level of pain. Animals are unrestrained and videoed using a handheld recording device and video images analyzed by an observer blinded to the drug treatment. At 8 and 12 hours post injury, corneas are evaluated using fluorescein to examine the wound area and animals are then sacrificed and eyes enucleated. Post mortem histology and histochemistry is used to examine corneal morphology and immune cell recruitment in all groups.

IV. Results

The inventors expect that the topical delivery of non-selective cannabinoids, $\Delta^9THC$, $\Delta^8THC$, WIN 55,212-2 and CP 55,940 will also reduce development of corneal hyperalgesia and allodynia and improve corneal wound healing after chemical burn via actions at both CB2 and CB1 receptors, respectively. Additionally, the inventors expect that these experiments will show that concomitant dosing with both topical CBD-DMH and the non-selective cannabinoids will result in improved therapeutic index (lower $ED_{50}$) for reducing corneal hyperalgesia and allodynia in wild-type animals. These actions will be reduced or absent in CB2 knock-out animals. Additionally, in animals lacking CB2, inflammation and hyperalgesia is expected to be exacerbated.

While the present disclosure has been described with reference to what are presently considered to be the examples, it is to be understood that the disclosure is not limited to the disclosed examples. Changes in form and substitution of equivalents are contemplated as circumstances might suggest or render expedient. These changes are to be understood within the spirit and scope of the appended claims. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

REFERENCES

Agarwal R., Iezhitsa I., Agarwal P., Abdul Nasir N. A., Razali N., Alyautdin R., Ismail N. M., Liposomes in topical ophthalmic drug delivery: an update. Drug Deliv. 2014 August 12:1-17.

Belmonte, C., M. C. Acosta and J. Gallar (2004). "Neural basis of sensation in intact and injured corneas." *Exp Eye Res* 78(3): 513-525.

Berenbaum, M. C. (1989). "What is synergy?" *Pharmacol Rev* 41(2): 93-141.

Conway, B. R. (2008). "Recent patents on ocular drug delivery systems." *Recent Pat Drug Deliv Formul* 2(1): 1-8.

Christopoulos, A. and T. Kenakin (2002). "G protein-coupled receptor allosterism and complexing." *Pharmacol Rev* 54(2): 323-374.

Daisuke Ito, Kortaro Tanaka, Shigeaki Suzuki, Tomohisa Dembo, and Yasuo Fukuuchi, "Enhanced Expression of Iba1, Ionized Calcium-Binding Adapter Molecule 1, After Transient Focal Cerebral Ischemia In Rat Brain" *Stroke*. 2001; 32:1208-1215.

Davis M P. Cannabinoids in pain management: CB1, CB2 and non-classic receptor ligands. Expert Opin Investig Drugs. 2014 August; 23(8):1123-40.

Draize, J. H., G. Woodard and H. O. Calvery (1944). "Methods for the study of irritation and toxicity of substances applied topically to the skin and mucous membranes." *J Pharmacol and Exp Therapeutics* 82: 377-390.

Frenzel, E. M., K. A. Neely, A. W. Walsh, J. D. Cameron and D. S. Gregerson (1998). "A new model of proliferative vitreoretinopathy." *Invest Ophthalmol Vis Sci* 39(11): 2157-2164.

Fride E, Feigin C, Ponde D E, Breuer A, Hanus L, Arshaysky N, Mechoulam R. (2004). "(+)-Cannabidiol analogues which bind cannabinoid receptors but exert peripheral activity only." *Eur J Pharmacol* 506(2): 179-188.

Friedman, N. J. (2010). "Impact of dry eye disease and treatment on quality of life." *Curr Opin Ophthalmol* 21(4): 310-316.

Guindon J., Hohmann A. G., Cannabinoid $CB_2$ receptors: a therapeutic target for the treatment of inflammatory and neuropathic pain. *British Journal of Pharmacology* 2008; 153:319-334.

Hanus, L., A. Breuer, S. Tchilibon, S. Shiloah, D. Goldenberg, M. Horowitz, R. G. Pertwee, R. A. Ross, M. R and E. Fride (1999). "HU-308: A specific agonist for CB2, a peripheral cannabinoid receptor." *Proc Nat Acad Sci* 96: 14228-14233.

Hohmann, A. G. and R. L. Suplita, 2nd (2006). "Endocannabinoid mechanisms of pain modulation." *AAPS J* 8(4): E693-708.

Hsieh, G. C., M. Pai, P. Chandran, B. A. Hooker, C. Z. Zhu, A. K. Salyers, E. J. Wensink, C. Zhan, W. A. Carroll, M. J. Dart, B. B. Yao, P. Honore and M. D. Meyer (2011). "Central and peripheral sites of action for CB(2) receptor mediated analgesic activity in chronic inflammatory and neuropathic pain models in rats." *Br J Pharmacol* 162(2): 428-440.

Hughes, P. M., O. Olejnik, J. E. Chang-Lin and C. G. Wilson (2005). "Topical and systemic drug delivery to the posterior segments." *Adv Drug Deliv Rev* 57(14): 2010-2032.

Jabs, D. A., R. B. Nussenblatt and J. T. Rosenbaum (2005). "Standardization of uveitis nomenclature for reporting clinical data. Results of the First International Workshop." *Am J Ophthalmol* 140(3): 509-516.

Laprairie R B, Bagher A M, Kelly M E M, Denovan-Wright E M (2014a). Cannabidiol is a negative allosteric modulator of the type 1 cannabinoid receptor (Brit. J. Pharmacol. Submitted).

Laprairie R B, Bagher A M, Kelly M E M, Dupre D J, Denovan-Wright E M (2014b). Type 1 Cannabinoid Receptor Ligands Display Functional Selectivity in a Cell Culture Model of Striatal Medium Spiny Projection Neurons. J Biol Chem E-pub ahead of print.

Lee, R. W. and A. D. Dick (2012). "Current concepts and future directions in the pathogenesis and treatment of non-infectious intraocular inflammation." *Eye (Lond)* 26(1): 17-28.

Ley, K., C. Laudanna, M. I. Cybulsky and S. Nourshargh (2007). "Getting to the site of inflammation: the leukocyte adhesion cascade updated." *Nat Rev Immunol* 7(9): 678-689.

Lobo, C. (2012). "Pseudophakic cystoid macular edema." *Ophthalmologica* 227(2): 61-67.

Loftsson, T. and D. Duchene (2007). "Cyclodextrins and their pharmaceutical applications." *Int J Pharm* 329(1-2): 1-11.

Loftsson, T. and E. Stefánsson (2002). "Cyclodextrins in eye drop formulations: enhanced topical delivery of corticosteroids to the eye." *Acta Ophthalmol Scand* 80(2): 144-150.

Maestrelli, F., M. L. Gonzalez-Rodriguez, A. M. Rabasco, C. Ghelardini and P. Mura (2010). "New "drug-in cyclodextrin-in deformable liposomes" formulations to improve the therapeutic efficacy of local anaesthetics." *Int J Pharm* 395(1-2): 222-231.

Maestrelli, F., M. L. Gonzalez-Rodriguez, A. M. Rabasco and P. Mura (2005). "Preparation and characterisation of liposomes encapsulating ketoprofen-cyclodextrin complexes for transdermal drug delivery." *Int J Pharm* 298(1): 55-67.

McPartland, J. M. and E. B. Russo (2001). "*Cannabis* and *cannabis* extracts, greater than the sum of their parts?" *J Cannabis Ther* 1(3-4): 103-132.

Mechoulam, R. and Hanus, L. (2002). "Cannabidiol: an overview of some chemical and pharmacological aspects. Part I: chemical aspects." *Chem Phys Lipids* 121(1-2): 35-43.

Natarajan J. V., Ang M., Darwitan A., Chattopadhyay S., Wong T. T., Venkatraman S. S., Nanomedicine for glaucoma: liposomes provide sustained release of latanoprost in the eye. Int J Nanomedicine. 2012; 7:123-31.

Oreja-Guevara C., Treatment of spasticity in multiple sclerosis: new perspectives regarding the use of cannabinoids. Rev Neurol. 2012a October 1; 55(7):421-30.

Oreja-Guevara C., Clinical efficacy and effectiveness of Sativex, a combined cannabinoid medicine, in multiple sclerosis-related spasticity. Expert Rev Neurother. 2012b April; 12(4 Suppl):3-8.

Pertwee R. G., The diverse $CB_1$ and $CB_2$ receptor pharmacology of three plant cannabinoids: $\Delta^9$-tetrahydrocannabinol, cannabidiol and $\Delta^9$-tetrahydrocannabivarin. *British Journal of Pharmacology* 2008; 153:199-215.

Pertwee R. G., Emerging strategies for exploiting cannabinoid receptor agonists as medicines. *British Journal of Pharmacology* 2009; 156:397-411.

Pertwee R. G., Targeting the endocannabinoid system with cannabinoid receptor agonists: pharmacological strategies and therapeutic possibilities. *Phil. Trans. R. Soc. B* 2012; 367:3353-3363.

Pflugfelder, S. C. (2008). "Prevalence, burden, and pharmacoeconomics of dry eye disease." *Am J Manag Care* 14(3 Suppl): S102-106.

Rahn, E. J. and A. G. Hohmann (2009). "Cannabinoids as pharmacotherapies for neuropathic pain: from the bench to the bedside." *Neurotherapeutics* 6(4): 713-737.

Ranta, V. P. and A. Urtti (2006). "Transscleral drug delivery to the posterior eye: prospects of pharmacokinetic modeling." *Adv Drug Deliv Rev* 58(11): 1164-1181. Rosenthal, P., I. Baran and D. S. Jacobs (2009). "Corneal pain without stain: is it real?" *Ocul Surf* 7(1): 28-40.

Rosenthal, P. and D. Borsook (2012). "The corneal pain system. Part I: the missing piece of the dry eye puzzle." *Ocul Surf* 10(1): 2-14.

Russo, E. B. (2011). "Taming THC: potential *cannabis* synergy and phytocannabinoid-terpenoid entourage effects." *Br J Pharm* 163: 1344-1364.

Sanz, M. J. and P. Kubes (2012). "Neutrophil-active chemokines in in vivo imaging of neutrophil trafficking." *Eur J Immunol* 42(2): 278-283.

Souto, E. B., S. Doktorovova, E. Gonzalez-Mira, M. A. Egea and M. L. Garcia (2010). "Feasibility of lipid nanoparticles for ocular delivery of anti-inflammatory drugs." *Curr Eye Res* 35(7): 537-552.

Straiker A J, Maguire G, Mackie K, Lindsey J. Localization of cannabinoid CB1 receptors in the human anterior eye and retina. Invest Ophthalmol Vis Sci. 1999; 40:2442-8.

Szczesniak, A. M., M. E. Kelly, S. Whynot, P. N. Shek and O. Hung (2006). "Ocular hypotensive effects of an intratracheally delivered liposomal delta9-tetrahydrocannabinol preparation in rats." *J Ocul Pharmacol Ther* 22(3): 160-167.

Szczesniak A, Kelly M E M (2012). Role of CB2 receptor in experimental uveoretinitis. International Cannabinoid Research Society 22nd Annual International Symposium on Cannabinoids, Frieburg, Germany.

Szczesniack A, Kelly M E M (2013). Role of CB2 receptor in experimental proliferative vitreoretinopathy. International Cannabinoid Research Society 23rd Annual International Symposium on Cannabinoids., Vancouver, BC.

Thumma, S., S. Majumdar, M. A. Elsohly, W. Gul and M. A. Repka (2008). "Preformulation studies of a prodrug of Delta9-tetrahydrocannabinol." *AAPS PharmSciTech* 9(3): 982-990.

Toguri, J. T., C. Lehmann, R. B. Laprairie, A. M. Szczesniak, J. Zhou, E. M. Denovan-Wright and M. E. Kelly (2014). "Anti-inflammatory effects of cannabinoid CB(2) receptor activation in endotoxin-induced uveitis." *Br J Pharmacol* 171(6): 1448-1461.

Wagner, H. and G. Ulrich-Merzenich (2009). "Synergy research: approaching a new generation of phytopharmaceuticals." *Phytomedicine* 16(2-3): 97-110.

Ward, S. J., M. D. Ramirez, H. Neelakantan and E. A. Walker (2011). "Cannabidiol prevents the development of cold and mechanical allodynia in paclitaxel-treated female C57B16 mice." *Anesth Analg* 113(4): 947-950.

Wenk, H. N. and C. N. Honda (2003). "Silver nitrate cauterization: characterization of a new model of corneal inflammation and hyperalgesia in rat." *Pain* 105(3): 393-401.

WO 2010041253 A1: Bab, I., R. Mechoulam, A. Breuer and N. Mussai. "Compositions comprising cb receptor agonists, uses thereof and methods for their preparation." Published: Apr. 15, 2010.

Yang Y., Yang H., Wang Z., Varadaraj K., Kumari S. S., Mergler S., Okada Y., Saika S., Kingsley P. J., Marnette L. J., Reinach P. S., Cannabinoid receptor 1 suppresses transient receptor potential vanilloid 1-induced inflammatory responses to corneal injury. *Cell Signal.* 2013; 25(2): 501-511.

Yanoof M and Duker J S, (2009). *Opthalmology.* Mosby Elsevier.

Yawn, B. P., P. C. Wollan, J. L. St Sauver and L. C. Butterfield (2013). "Herpes zoster eye complications: rates and trends." *Mayo Clin Proc* 88(6): 562-570.

The invention claimed is:

1. A method of treating ocular inflammation and/or ocular neuropathic pain in a subject in need thereof, comprising administering ocularly to the subject a CB2 positive allosteric modulator.

2. The method of claim 1, wherein the CB2 positive allosteric modulator is CBD-DMH.

3. The method of claim 2, wherein the method comprises administering the CBD-DMH in combination with at least one further CB2 target agent.

4. The method of claim 3, wherein the at least one further CB2 target agent is HU 433, HU 308, β-caryophyllene, CBD or combinations thereof.

5. The method of claim 2, wherein the method comprises administering the CBD-DMH in combination with at least one further cannabimimetic agent.

6. The method of claim 5, wherein the at least one further cannabimimetic agent is a non-selective cannabinoid receptor agonist.

7. The method of claim 6, wherein the non-selective cannabinoid receptor agonist is selected from $\Delta^8$-THC or a prodrug thereof, $\Delta^9$-THC or a prodrug thereof, CP 55,940, WIN 55,212-2 and combinations thereof.

8. The method of claim 1, wherein the method is a method of treating ocular inflammation caused by a non-infectious condition.

9. The method of claim 8, wherein the condition is selected from posterior uveitis, retinitis, uveoretinitis and proliferative vitreoretinopathy.

10. The method of claim 8, wherein the ocular inflammation further presents with non-neuropathic pain and the treatment reduces the pain.

11. The method of claim 10, wherein the condition is selected from anterior uveitis, episcleritis and scleritis.

12. The method of claim 3, wherein the ocular inflammation is intraocular inflammation.

13. The method of claim 6, wherein the method is a method for treating ocular neuropathic pain and ocular inflammation caused by a non-infectious condition.

14. The method of claim 13, wherein the ocular neuropathic pain arises from dry eye, trauma, a corneal abrasion, a corneal burn, a corneal transplant, an autoimmune disease or an allergen.

15. An ocular pharmaceutical composition comprising a CB2 positive allosteric modulator and a carrier suitable for ocular administration to an eye.

16. The composition of claim 15, wherein the CB2 positive allosteric modulator is CBD-DMH.

17. The composition of claim 16, wherein the composition comprises at least one further CB2 target agent.

18. The composition of claim 16, wherein the composition further comprises at least one further cannabimimetic agent.

19. The composition of claim 15, wherein the carrier comprises a liposome.

20. The method of claim 2, wherein the method comprises administering the CBD-DMH in combination with at least one further CB2 target agent, at least one further cannabimimetic agent or combinations thereof.

21. The composition of claim 16, wherein the composition comprises at least one further CB2 target agent, at least one further cannabimimetic agent or combinations thereof.

22. The method of claim 2, wherein the CBD-DMH is administered topically.

23. The composition of claim 16, wherein the composition is a topical ocular pharmaceutical composition and the carrier is suitable for topical administration to the eye.

* * * * *